(12) United States Patent
Abe

(10) Patent No.: US 8,270,681 B2
(45) Date of Patent: Sep. 18, 2012

(54) VEIN PATTERN MANAGEMENT SYSTEM, VEIN PATTERN REGISTRATION APPARATUS, VEIN PATTERN AUTHENTICATION APPARATUS, VEIN PATTERN REGISTRATION METHOD, VEIN PATTERN AUTHENTICATION METHOD, PROGRAM, AND VEIN DATA CONFIGURATION

(75) Inventor: Hiroshi Abe, Tokyo (JP)

(73) Assignee: Sony Corporation, Tokyo (JP)

( * ) Notice: Subject to any disclaimer, the term of this patent is extended or adjusted under 35 U.S.C. 154(b) by 393 days.

(21) Appl. No.: 12/600,045

(22) PCT Filed: Apr. 24, 2008

(86) PCT No.: PCT/JP2008/057952
§ 371 (c)(1),
(2), (4) Date: Nov. 13, 2009

(87) PCT Pub. No.: WO2008/139884
PCT Pub. Date: Nov. 20, 2008

(65) Prior Publication Data
US 2010/0208948 A1    Aug. 19, 2010

(30) Foreign Application Priority Data

May 16, 2007 (JP) .................. 2007-130841

(51) Int. Cl.
*G06K 9/00* (2006.01)
(52) U.S. Cl. ....................... 382/115; 382/117
(58) Field of Classification Search .......... None
See application file for complete search history.

(56) References Cited

U.S. PATENT DOCUMENTS

| 7,450,757 B2 * | 11/2008 | Kato et al. ............ 382/172 |
| 2005/0047632 A1 * | 3/2005 | Miura et al. ............ 382/124 |
| 2009/0129635 A1 * | 5/2009 | Abe ..................... 382/115 |
| 2010/0215223 A1 * | 8/2010 | Abe ..................... 382/115 |

FOREIGN PATENT DOCUMENTS

| JP | 2005-56282 | 3/2005 |
| JP | 2005-71118 | 3/2005 |
| JP | 2005-259345 | 9/2005 |
| JP | 2007-72676 | 3/2007 |

OTHER PUBLICATIONS

T. Matsumoto, "Biometric Authentication in Financial Transactions", 9th Study Group on Problem of Forged ATM Cards, Financial Services Agency, pp. 1-32 (2005).

\* cited by examiner

*Primary Examiner* — Chan S Park
*Assistant Examiner* — Nancy Bitar
(74) *Attorney, Agent, or Firm* — Finnegan, Henderson, Farabow, Garrett & Dunner, L.L.P.

(57) ABSTRACT

There are provided an imaging unit for capturing an image of a portion of a body surface of a living body with near-infrared light and generating near-infrared light imaging data, a vein pattern extraction unit for extracting a vein pattern from the near-infrared light imaging data by applying a differential filter, which outputs a large value for a pixel having a large difference between the pixel and its surrounding pixel, to a plurality of pixels constituting the near-infrared light imaging data, and a pseudo-vein pattern determination unit for determining presence of a pseudo-vein pattern intentionally formed on a part of the captured body surface based on the extracted vein pattern.

5 Claims, 12 Drawing Sheets

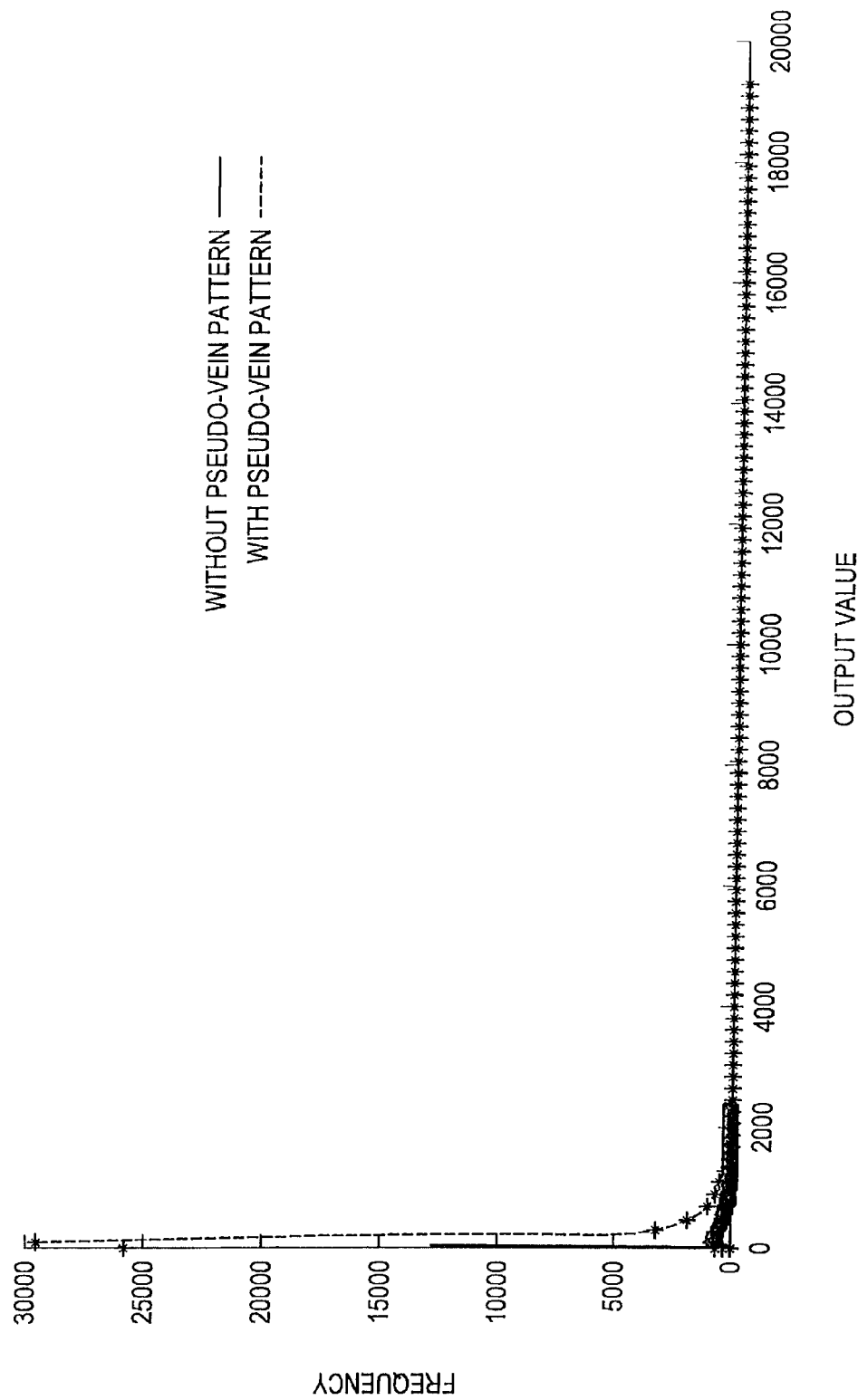

VEIN PATTERN MANAGEMENT SYSTEM, VEIN PATTERN REGISTRATION APPARATUS, VEIN PATTERN AUTHENTICATION APPARATUS, VEIN PATTERN REGISTRATION METHOD, VEIN PATTERN AUTHENTICATION METHOD, PROGRAM, AND VEIN DATA CONFIGURATION

CROSS REFERENCE TO RELATED APPLICATIONS

This application is a national phase application based on PCT/JP2008/057952, filed Apr. 24, 2008, which claims the priority of Japanese Patent Application No. 2007-130841, filed May 16, 2007, the contents of all of which are incorporated herein by reference.

TECHNICAL FIELD

The present invention relates to a vein pattern management system, a vein pattern registration apparatus, a vein pattern authentication apparatus, a vein pattern registration method, a vein pattern authentication method, a program, and a vein data configuration.

BACKGROUND ART

Individual authentication methods include a method for authenticating an individual by registering a fingerprint, a voiceprint, an iris, and a retina of the individual, or a vein pattern of the back of the individual's hand or the individual's finger, or the like as registered data in advance, and verifying and determining data input at the time of authentication and the registered data. In particular, individual authentication using the vein pattern has recently been focused on due to its high discriminating ability.

For the purpose of improving security of the above-mentioned individual authentication methods, since it is essential to block illegal users attempting to impersonate normal authenticated users, methods for blocking such illegal users have been widely developed (for example, refer to Patent Document 1 and Non-Patent Document 1).

PRIOR ART DOCUMENT

[Patent Document 1] Japanese Patent Application Publication No. 2005-259345
[Non-Patent Document 1] Tsutomu Matsumoto, "Biometric Authentication in Financial Transactions", the 9th Study Group on Problem of Forged ATM Cards", Financial Services Agency, Apr. 15, 2005

In some individual authentication methods using a vein pattern, the vein pattern is extracted by capturing an image of a backside or a finger of a hand with near-infrared light and processing extracted imaging data using a differential filter.

However, since the differential filter used to the imaging data captured with the near-infrared light into a vein portion and a non-vein portion is apt to output a pseudo-vein pattern, which has been drawn on a body surface with a felt-tip pen and the like, as a vein portion, there is a need for a method for determining presence of such a pseudo-vein pattern in order to avoid impersonation by an illegal user.

The present invention has been made in consideration of the above-mentioned problems, and an object of the present invention is to provide a novel and improved vein pattern management system, vein pattern registration apparatus, vein pattern authentication apparatus, vein pattern registration method, vein pattern authentication method, program, and vein data configuration, capable of determining presence of a pseudo-vein pattern intentionally produced on a body surface.

DISCLOSURE OF THE INVENTION

In order to solve the above problem, according to an embodiment of the invention, there is provided a vein pattern management system for registering and authenticating a vein pattern acquired by radiating light to a portion of a living body, including: an imaging unit for capturing an image of a body surface of the portion of the living body with near-infrared light and generating near-infrared light imaging data; a vein pattern extraction unit for extracting a vein pattern from the near-infrared light imaging data by applying a differential filter, which outputs a large value for a pixel having a large difference between the pixel and its surrounding pixel, to a plurality of pixels constituting the near-infrared light imaging data; a pseudo-vein pattern determination unit for determining presence of a pseudo-vein pattern intentionally formed on a part of the captured body surface based on the extracted vein pattern; a vein pattern registration unit for registering the near-infrared light vein pattern based on a determination result from the determination unit to generate a registered vein pattern; and a vein pattern authentication unit for comparing a newly generated near-infrared light vein pattern with the registered vein pattern based on the determination result from the pseudo-vein pattern determination unit and authenticating the newly generated near-infrared vein pattern, wherein the vein pattern extraction unit calculates a distribution of output values based on acquired output values of the differential filter, and the pseudo-vein pattern determination unit determines the presence of the pseudo-vein pattern based on the distribution of the output values.

In order to solve the above problem, according to another embodiment of the invention, there is provided a vein pattern registration apparatus including: an imaging unit for capturing an image of a body surface of a portion of a living body with near-infrared light and generating near-infrared light imaging data; a vein pattern extraction unit for extracting a vein pattern from the near-infrared light imaging data by applying a differential filter, which outputs a large value for a pixel having a large difference between the pixel and its surrounding pixel, to a plurality of pixels constituting the near-infrared light imaging data; a pseudo-vein pattern determination unit for determining presence of a pseudo-vein pattern intentionally formed on a part of the captured body surface based on the extracted vein pattern; and a vein pattern registration unit for registering the near-infrared light vein pattern based on a determination result from the determination unit to generate a registered vein pattern, wherein the vein pattern extraction unit calculates a distribution of output values based on acquired output values of the differential filter, and the pseudo-vein pattern determination unit determines the presence of the pseudo-vein pattern based on the distribution of the output values.

In order to solve the above problem, according to still another embodiment of the invention, there is provided a vein pattern authentication apparatus including: an imaging unit for capturing an image of a body surface of a portion of a living body with near-infrared light and generating near-infrared light imaging data; a vein pattern extraction unit for extracting a vein pattern from the near-infrared light imaging data by applying a differential filter, which outputs a large value for a pixel having a large difference between the pixel and its surrounding pixel, to a plurality of pixels constituting the near-infrared light imaging data; a pseudo-vein pattern determination unit for determining presence of a pseudo-vein pattern intentionally formed on a part of the captured body surface based on the extracted vein pattern; and a vein pattern authentication unit for comparing the captured near-infrared light vein pattern with an already registered vein pattern and authenticating the captured near-infrared light vein pattern based on a determination result from the pseudo-vein pattern determination unit, wherein the vein pattern extraction unit calculates a distribution of output values based on acquired output values of the acquired differential filter, and the pseudo-vein pattern determination unit determines the presence of the pseudo-vein pattern based on the distribution of the output values.

The vein pattern extraction unit may further include an output estimation value calculation unit for calculating an output estimation value indicating a ratio of a sum of output values, which are more than a predetermined upper output value, among acquired output values of the differential filter relative to a total sum of the acquired output values of the differential filter, and the pseudo-vein pattern determination unit may determine the presence of the pseudo-vein pattern based on the output estimation value.

The pseudo-vein pattern determination unit may determine that the pseudo-vein pattern is present when the output estimation value is more than a predetermined threshold value, and determine that the pseudo-vein pattern is not present when the output estimation value is less than the predetermined threshold value.

The differential filter may be a derivative filter or a Laplacian of Gaussian (Log) filter.

The vein pattern authentication unit may authenticate the near-infrared light vein pattern based on the registered vein pattern acquired from a vein pattern registration apparatus and authenticate the near-infrared light vein pattern based on the registered vein pattern registered within the vein pattern authentication apparatus.

In order to solve the above problem, according to still another embodiment of the invention, there is provided a vein pattern registration method for registering a vein pattern acquired by radiating light to a portion of a living body, including the steps of: capturing an image of a body surface of the portion of the living body with near-infrared light and generating near-infrared light imaging data; extracting a vein pattern from the near-infrared light imaging data to generate a near-infrared light vein pattern by applying a differential filter, which outputs a large value for a pixel having a large difference between the pixel and its surrounding pixel, to a plurality of pixels constituting the near-infrared light imaging data; calculating a distribution of output values based on the output values of the differential filter; determining presence of a pseudo-vein pattern intentionally formed on a part of the captured body surface based on the calculated distribution of the output values; and registering the vein pattern as a registered vein pattern based on a determination result.

In order to solve the above problem, according to still another embodiment of the invention, there is provided a vein pattern authentication method for authenticating a vein pattern acquired by radiating light to a portion of a living body, including the steps of: capturing an image of a body surface of the portion of the living body with near-infrared light and generating near-infrared light imaging data; extracting a vein pattern from the near-infrared light imaging data to generate a near-infrared light vein pattern by applying a differential filter, which outputs a large value for a pixel having a large difference between the pixel and its surrounding pixel, to a plurality of pixels constituting the near-infrared light imaging data; calculating a distribution of output values based on the output values of the differential filter; determining presence of a pseudo-vein pattern intentionally formed on a part of the captured body surface based on the calculated distribution of the output values; and comparing an already registered vein pattern with the near-infrared light vein pattern and authenticating the near-infrared light vein pattern based on a determination result.

In the step of calculating a distribution of output values, an output estimation value indicating a ratio of a sum of output values, which are more than a predetermined upper output value, may be calculated among acquired output values of the differential filter relative to a total sum of the acquired output values of the differential filter.

In the step of determining presence of a pseudo-vein pattern, it may be determined that the pseudo-vein pattern is present when the output estimation value is more than a predetermined threshold value, and it may be determined that the pseudo-vein pattern is not present when the output estimation value is less than the predetermined threshold value.

The differential filter may be a derivative filter or a Laplacian of Gaussian (Log) filter.

In order to solve the above problem, according to still another embodiment of the invention, there is provided a program for causing a computer controlling a vein pattern registration apparatus for registering a vein pattern acquired by radiating light to a portion of a living body to execute: an imaging function for capturing an image of a body surface of the portion of the living body with near-infrared light and generating near-infrared light imaging data; a vein pattern extraction function for extracting a vein pattern from the near-infrared light imaging data by applying a differential filter, which outputs a large value for a pixel having a large difference between the pixel and its surrounding pixel, to a plurality of pixels constituting the near-infrared light imaging data and at the same time, calculating a distribution of output values based on acquired output values of the differential filter; a pseudo-vein pattern determination function for determining presence of a pseudo-vein pattern intentionally formed on a part of the captured body surface based on the distribution of the output values for the extracted vein pattern; and a vein pattern registration function for registering the near-infrared light vein pattern based on a determination result to generate a registered vein pattern.

According to this configuration, a computer program is stored in a storage unit included in a computer, and read and executed by CPU included in the computer so that the computer program causes the computer to operate as the above-mentioned vein pattern registration apparatus. In addition, there can be also provided a computer readable recording medium in which the computer program is recorded. The recording medium may be, for example, a magnetic disk, an optical disk, a magnetic optical disk, a flush memory, and the like. Furthermore, the above-mentioned computer program may be distributed via a network without using a recording medium.

In order to solve the above problem, according to still another embodiment of the invention, there is provided a program for causing a computer controlling a vein pattern authentication apparatus for authenticating a vein pattern acquired by radiating light to a portion of a living body to execute: an imaging function for capturing an image of a body surface of the portion of the living body with near-infrared light and generating near-infrared light imaging data; a vein pattern extraction function for extracting a vein pattern from the near-infrared light imaging data by applying a differential filter, which outputs a large value for a pixel having a large difference between the pixel and its surrounding pixel, to a plurality of pixels constituting the near-infrared light imaging data and at the same time, calculating a distribution of output values based on acquired output values of the differential filter; a pseudo-vein pattern determination function for determining presence of a pseudo-vein pattern intentionally formed on a part of the captured body surface based on the distribution of the output values for the extracted vein pattern; and a vein pattern authentication function for comparing the captured near-infrared light vein pattern with an already registered vein pattern and authenticating the captured near-infrared imaging pattern based on a determination result.

According to this configuration, a computer program is stored in a storage unit included in a computer, and read and executed by CPU included in the computer so that the computer program causes the computer to operate as the above-mentioned vein pattern registration apparatus. In addition, there can be also provided a computer readable recording medium in which the computer program is recorded. The recording medium may be, for example, a magnetic disk, an optical disk, a magnetic optical disk, a flush memory, and the like. Furthermore, the above-mentioned computer program may be distributed via a network without using a recording medium.

In order to solve the above problem, according to still another embodiment of the invention, there is provided a vein data configuration including: a vein data storage area containing data that correspond to a vein pattern of an individual and are to be verified with image data acquired by capturing an image of a part of a body surface of a living body with near-infrared light; and an output estimation value storage area containing an evaluated output value indicating a ratio of a sum of output values, which are more than a predetermined upper output value, among output values of a differential filter relative to a total sum of the output values of the differential filter for the image data acquired by capturing the image with the near-infrared light, wherein the differential filter is a filter outputting a large value for a pixel having a large difference between the pixel and its surrounding pixel for each pixel constituting the image data acquired by capturing the image with the near-infrared light.

The vein data configuration may further include a parameter storage area containing a parameter changing an output property of the differential filter, and the parameter significantly may change an output value of the differential filter, when the image data acquired by capturing the image with the near-infrared light have a difference greater than that between a value indicating a vein portion and a value indicating a non-vein portion.

According to embodiments of the present invention, presence of a pseudo-vein pattern intentionally produced on a body surface can be determined.

BRIEF DESCRIPTION OF THE DRAWINGS

FIG. 3 is an explanatory diagram illustrating an output value distribution of a Log filter;

EXPLANATION OF NUMERAL

Figure 1A:
FIG. 1A is an explanatory diagram illustrating an output value of a Log filter for a vein pattern.

10 Vein pattern management system
12 Network
14 Removable recording medium
20 Vein pattern registration apparatus
30 Vein pattern authentication apparatus
201 CPU
203 ROM
205 RAM
207 BUS
211 Imaging device
213 Input device
215 Output device
217 Storage device
219 Drive
221 Communication device
231, 301 Imaging unit
233, 303 Radiation unit
235, 305 Near-infrared light
237, 307 Optical lens
239, 309 Imaging data generation unit
241, 311 Vein pattern extraction unit
243, 313 Output estimation value calculation unit
251, 321 Pseudo-vein pattern determination unit
261, 331 Vein pattern registration unit
263, 333 Storage unit
265 Registered vein pattern disclosure unit

BEST MODE FOR CARRYING OUT THE INVENTION

First Embodiment

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

Although, in a later description, the present invention will be described in connection with an example of vein patterns of fingers, the present invention is not limited to this example.

<Pseudo-Vein Pattern>

A pseudo-vein pattern intentionally formed on a finger surface will be described as an example of pseudo-vein patterns in preparation for a description of a vein pattern management system according to a first embodiment of the present invention.

In biometric authentication with finger vein pattern, although impersonation is difficult because a vein pattern itself is located inside of a finger, it is also difficult, in extraction of the vein pattern, to determine whether an extracted vein pattern is located inside of the finger. Since a vein per se absorbs near-infrared light, the vein is imaged as a dark shadow while capturing an image of a body surface, and if a pseudo-vein pattern is drawn on the body surface with a component, which has absorbency similar to that of the vein, the pseudo-vein pattern might be indistinguishable from the vein pattern.

Since the near-infrared light is permeable to body tissue, on one hand, and is absorbable in hemoglobin in blood (reduced hemoglobin), on the other hand, veins distributed inside of a finger, a palm of a hand, or a back of a hand appear as shadows in an image when the near-infrared light is radiated to the finger, the palm of the hand, or the back of the hand. The shadows of the vein appearing on the image are referred to as a vein pattern.

Figure 9:
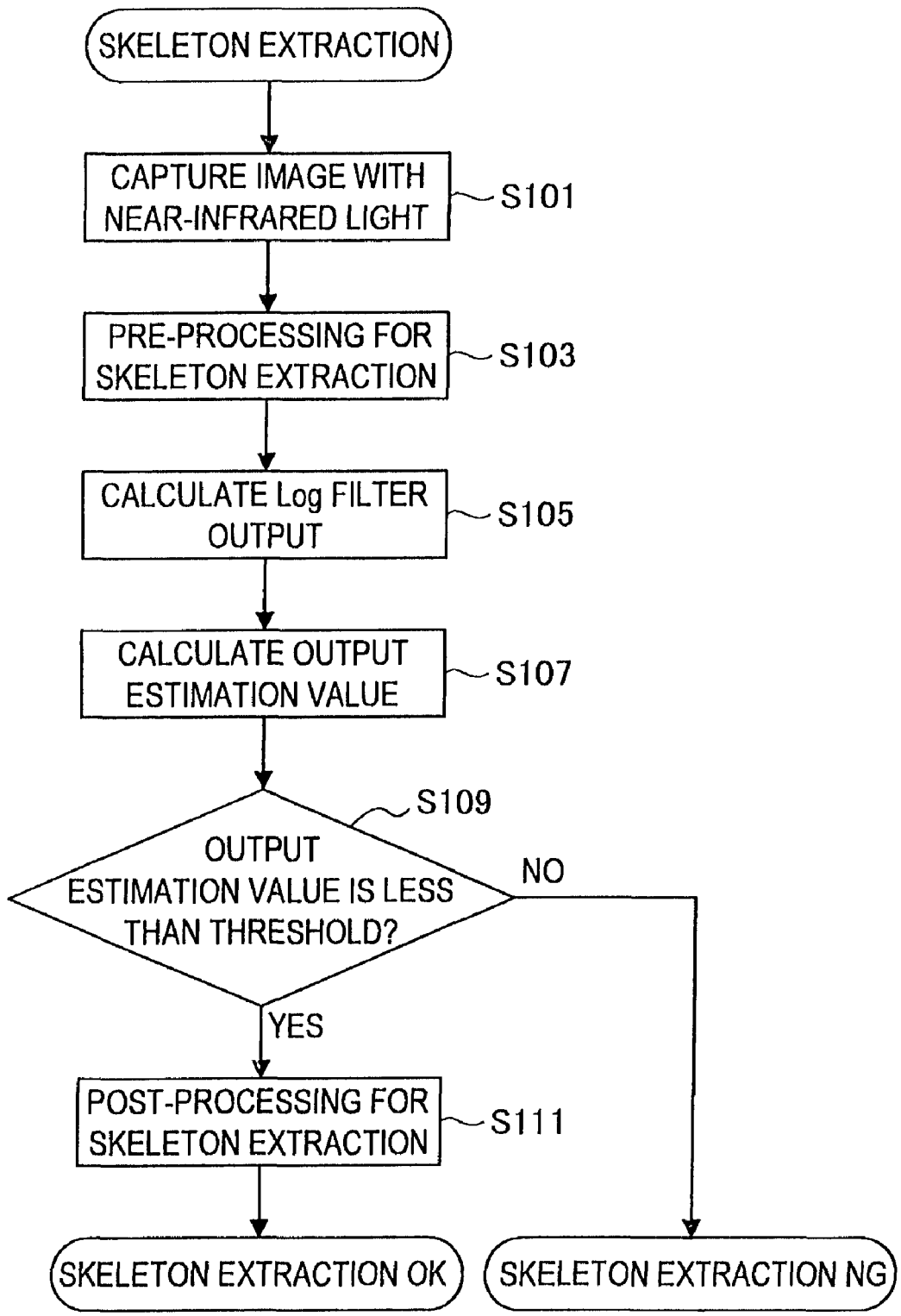
FIG. 9 is a flowchart illustrating a skeleton extracting method according to the embodiment.
Figure 10:
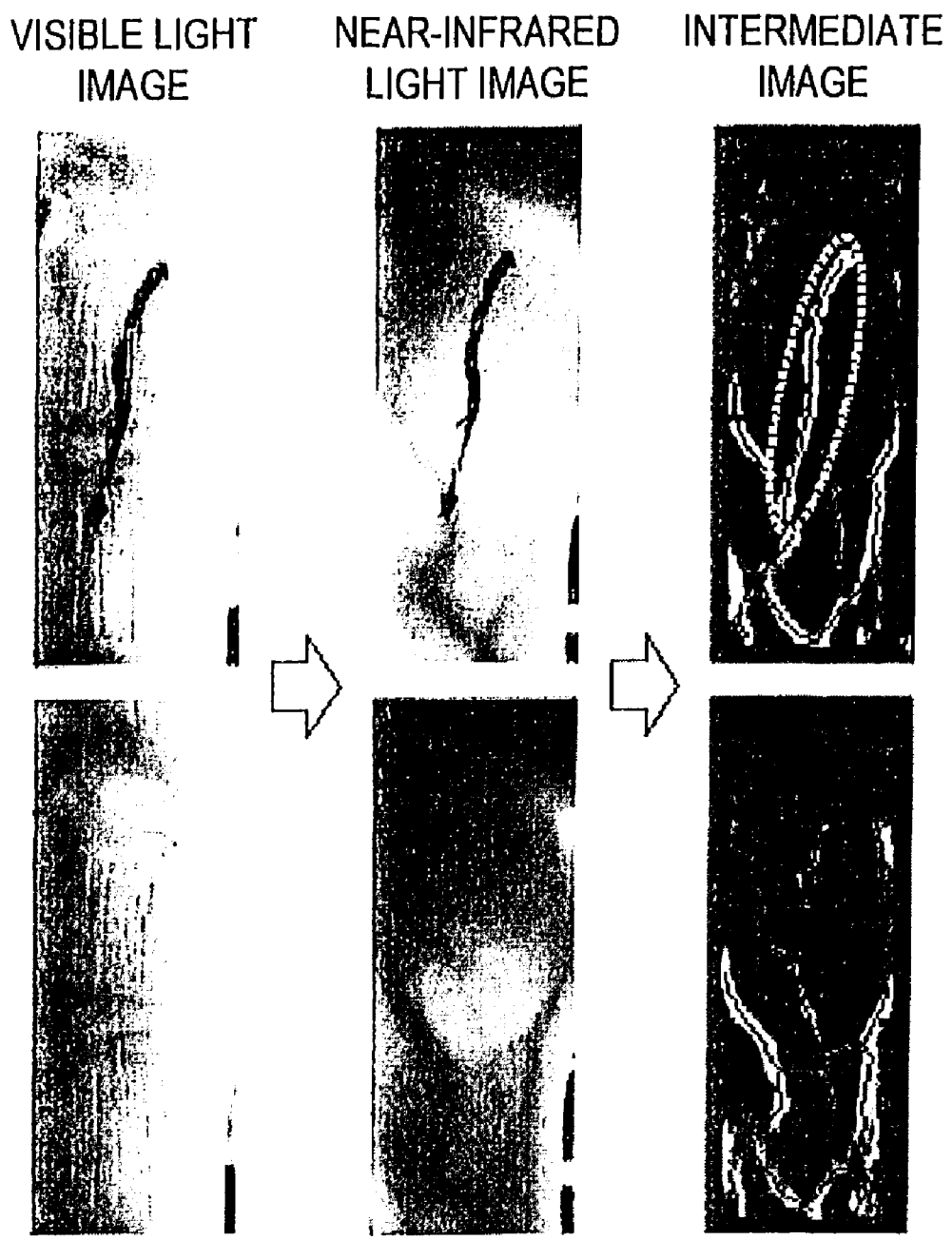
FIG. 10 is an explanatory diagram illustrating a pseudo-vein pattern drawn on a finger surface.

FIG. 10 is an explanatory diagram illustrating a pseudo-vein pattern drawn on a finger surface. The upper part of FIG. 10 represents a case in which a pseudo-vein pattern is directly drawn on a finger surface with a permanent pen, and the lower part of FIG. 9 represents a case in which no pseudo-vein patterns are drawn on the finger surface. In addition, in either of the upper and lower parts, there are shown from left to right a captured image with visible light, a captured image with near-infrared light, and an image subject to a threshold process of an output of a Laplacian of Gaussian (Log) filter that is a kind of differential filters, respectively.

The threshold process as used herein refers to a process in which predetermined upper and lower threshold values are assigned to an output value of a Log filter and the output value is set to zero if the output value is less than the lower threshold value and the output value is set to the upper threshold value if the output value is greater than the upper threshold value.

Since an ink component of the permanent pen has a light absorption property similar to that of reduced hemoglobin in a vein, the pseudo-vein pattern drawn with the permanent pen is left in an intermediate image not yet subject to a thinning process as a vein pattern, as shown in top right and bottom right ends of FIG. 10, and is ultimately recognized as a vein in the finger.

In order to solve such problems, the inventors of this application has been dedicated to developing so that the inventor has contrived a vein pattern management system, an vein pattern registration apparatus, a vein pattern authentication apparatus, a vein pattern registration method, a vein pattern authentication method, a program, and a vein data configuration.

Present Embodiment

Output Value of Differential Filter

Figure 1B:
FIG. 1B is an explanatory diagram illustrating an output value of a Log filter for a vein pattern.
Figure 1C:
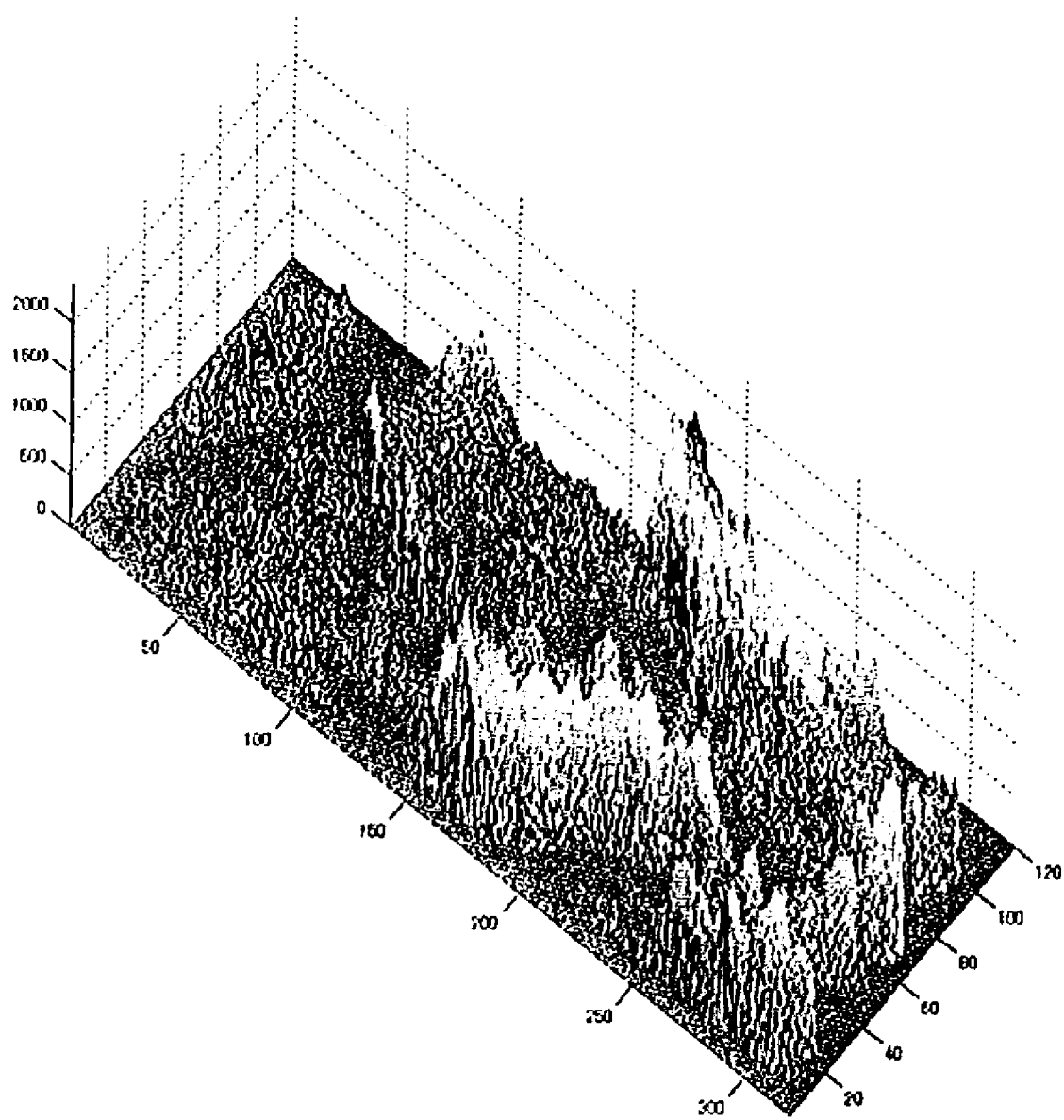
FIG. 1C is an explanatory diagram illustrating an output value of a Log filter for a vein pattern.

Referring to FIGS. 1A to 1C, near-infrared light imaging data acquired by capturing an image of a finger surface with near-infrared light and an output value of a Log filter for a near-infrared light vein pattern acquired by extracting a vein pattern from the near-infrared light imaging data and applying a Log filter, which is a kind of differential filters, to the near-infrared light vein pattern, will be described in detail. FIGS. 1A to 1C are explanatory diagrams illustrating an output value of the Log filter for a vein pattern.

FIG. 1A shows near-infrared light imaging data, FIG. 1B shows a Log filter output for a near-infrared light vein pattern, and FIG. 1C shows a three dimensional representation of the Log filter output. In addition, the Log filter output in FIG. 1B has been subject to a threshold process. As shown in FIG. 1A, because the near-infrared light is absorbable in hemoglobin in blood, a finger vein portion is imaged as a dark shadow in the near-infrared light imaging data. Therefore, the application of a differential filter, such as a Log filter, to the imaging data makes it possible to show a clear contrast between the finger vein portion and others, and to allow the finger vein portion to be remarkably visible, as shown in FIG. 1B. With reference to the three dimensional representation of the Log filter output shown in FIG. 1C, it can be seen that the finger vein portion imaged as a white portion in output values of the Log filter has output magnitude up to approximately 2,000, which is relatively higher than that of the others.

Figure 2A:
FIG. 2A is an explanatory diagram illustrating an output value of a Log filter for a vein pattern.
Figure 2B:
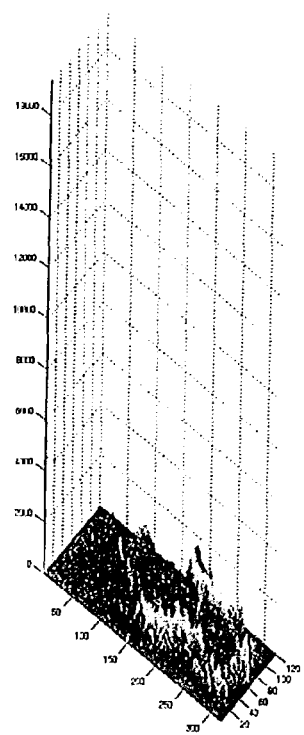
FIG. 2B is an explanatory diagram illustrating an output value of a Log filter for a vein pattern.
Figure 2C:
FIG. 2C is an explanatory diagram illustrating an output value of a Log filter for a vein pattern.
Figure 2D:
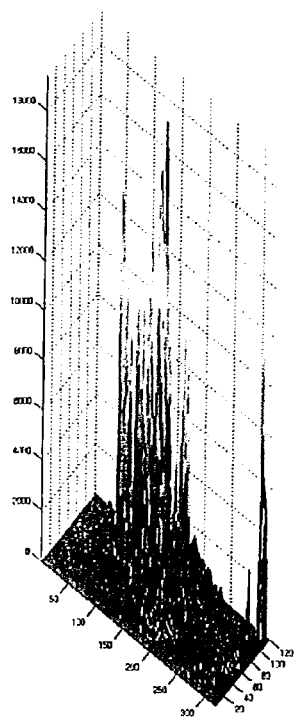
FIG. 2D is an explanatory diagram illustrating an output value of a Log filter for a vein pattern.

Now referring to FIGS. 2A to 2D, a Log filter output in presence of a pseudo-vein pattern on a finger surface will be considered. FIGS. 2A to 2D are explanatory diagrams illustrating a Log file output value for a vein pattern. FIG. 2A shows a Log filter output in absence of a pseudo-vein pattern on a finger surface, and FIG. 2B shows a three dimensional representation of the Log filter output. FIG. 2C shows a Log filter output in presence of a pseudo-vein pattern on the finger surface, and FIG. 2D shows a three dimensional representation of the Log filter output. In FIGS. 2A and 2C, for convenience of comparison, a threshold process has been applied to the Log filter output. To the contrary, in FIGS. 2B and 2C, there is shown the Log filter output to which the threshold process has not been applied.

Referring to FIGS. 2C and 2D, it can be seen that the Log filter output value for a portion with the pseudo-vein pattern exceeds approximately 18,000 and is remarkably visible relative to a finger vein portion. This is because, differently from a vein contained inside of a finger, as the pseudo-vein pattern is formed on the finger surface, a significantly high contrast appears between the pseudo-vein pattern and its surrounding and the pseudo-vein pattern responds sensitively to a Log filter.

Based on the above-mentioned knowledge, the inventor of the present application has focused attention on an output value of a differential filter, such as a Log filter, so that the inventor has conceived that presence of a pseudo-vein pattern formed on a finger surface can be detected.

FIG. 3 shows a distribution of output values of a Log filter shown in FIGS. 2B and 2D. In FIG. 3, an output value of the Log filter is taken as an abscissa axis and a frequency is taken as an ordinate axis.

As can be seen from FIG. 3, in presence of a pseudo-vein pattern on a finger surface, output values of a Log filter extend close to 20,000, whereas, in absence of the pseudo-vein pattern, the output values of the Log filter extend slightly around 2,000. This means that the presence of the pseudo-vein pattern on the finger surface allows the output values of the Log filter to reach a very high value and have a remarkably different distribution of output values of a Log filter.

With this point in view, in order to readily estimate a distribution of output values of a differential filter, such as a Log filter, the inventor of the present application has conceived a method of defining an output estimation value of the differential filter, as described later, and determining presence of a pseudo-vein pattern based on the output estimation value.

The output estimation value of the differential filter is defined as Equation 1 as follows. In Equation 1, $v^{thr}$ represents an upper output value of the differential filter, $S(v^{thr})$ represents a sum of output values more than the upper output value $v^{thr}$ of the differential filter, and $r(v^{thr})$ represents an output estimation value. In addition, S(0) indicates a sum of the output values of the differential filter when the upper output value of the differential filter satisfies $v^{thr}=0$ and also indicates a simple total sum of the output values of the differential filter.

It is noted that the above-mentioned $v^{thr}$ is a value which has been previously set based on an output value distribution of the differential filter calculated from a prior determination test or the like using multiple estimation data.

$$r(v^{thr}) = \frac{S(v^{thr})}{S(0)} \quad (1)$$

Figure 4:
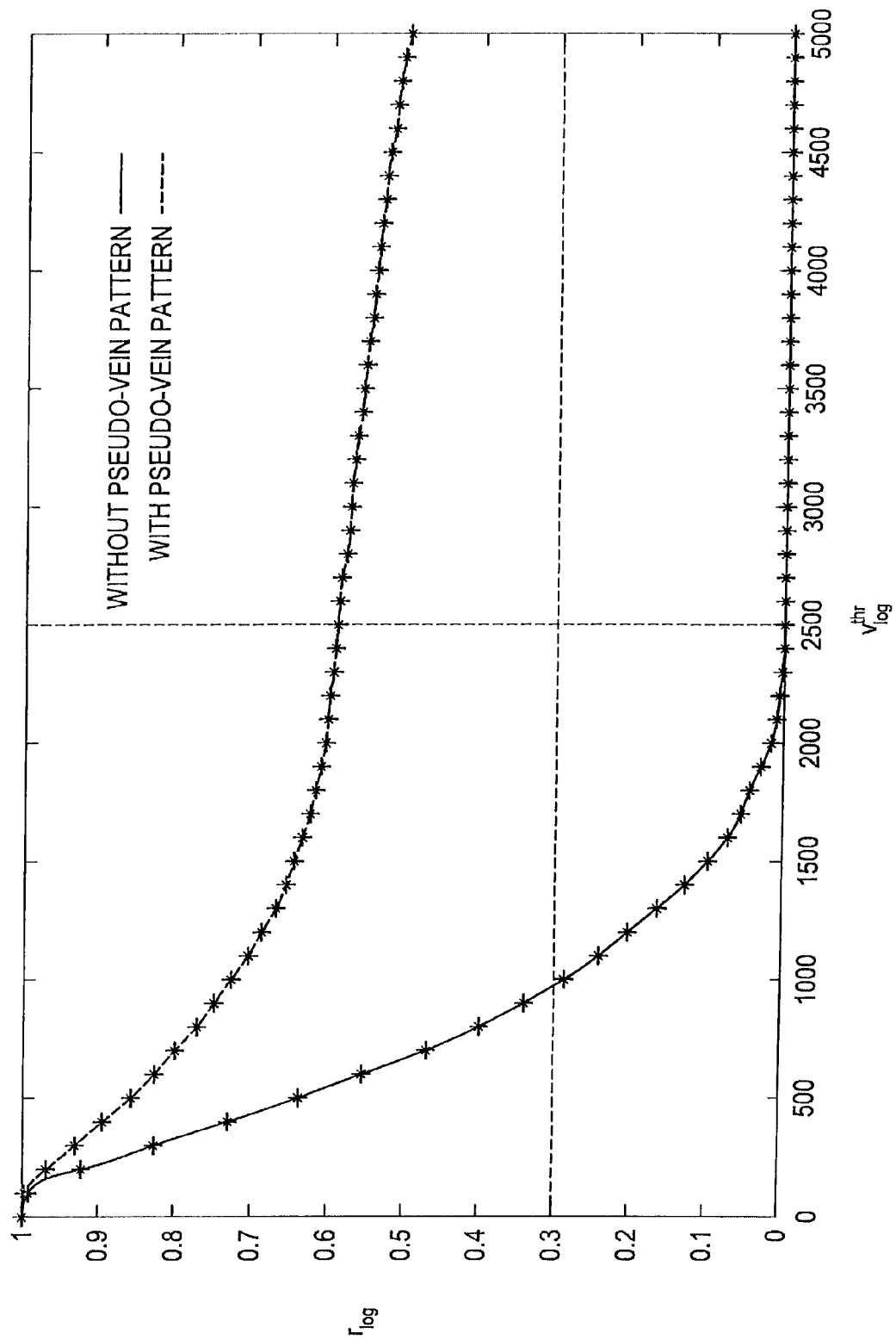
FIG. 4 is a diagram illustrating a variation of an output estimation value of a Log filter.

The output estimation value was calculated for the Log filter output illustrated in FIGS. 2B and 2D, and a result of this calculation is shown in FIG. 4. FIG. 4 is a graph illustrating a variation in the output estimation value of the Log filter. In FIG. 4, an upper output value is taken as an abscissa axis and an output estimation value is taken as an ordinate axis.

Referring to FIG. 4, it is appreciated that, in absence of a pseudo-vein pattern, an upper output value is approximately 2,500 and an output estimation value is approximately 0, whereas, in presence of the pseudo-vein pattern, although the upper output value is 5,000, the output estimation value remains large.

As is apparent from FIG. 4, presence of the pseudo-vein pattern can be determined by setting the upper output value to approximately 2,500, for example, and setting the output estimation value to approximately 0.3. It should be noted that a threshold of the upper output value and a threshold of the output estimation value are merely one example and the threshold of the upper output value may be individually set for each particular individual.

(Vein Pattern Management System)

Figure 5:
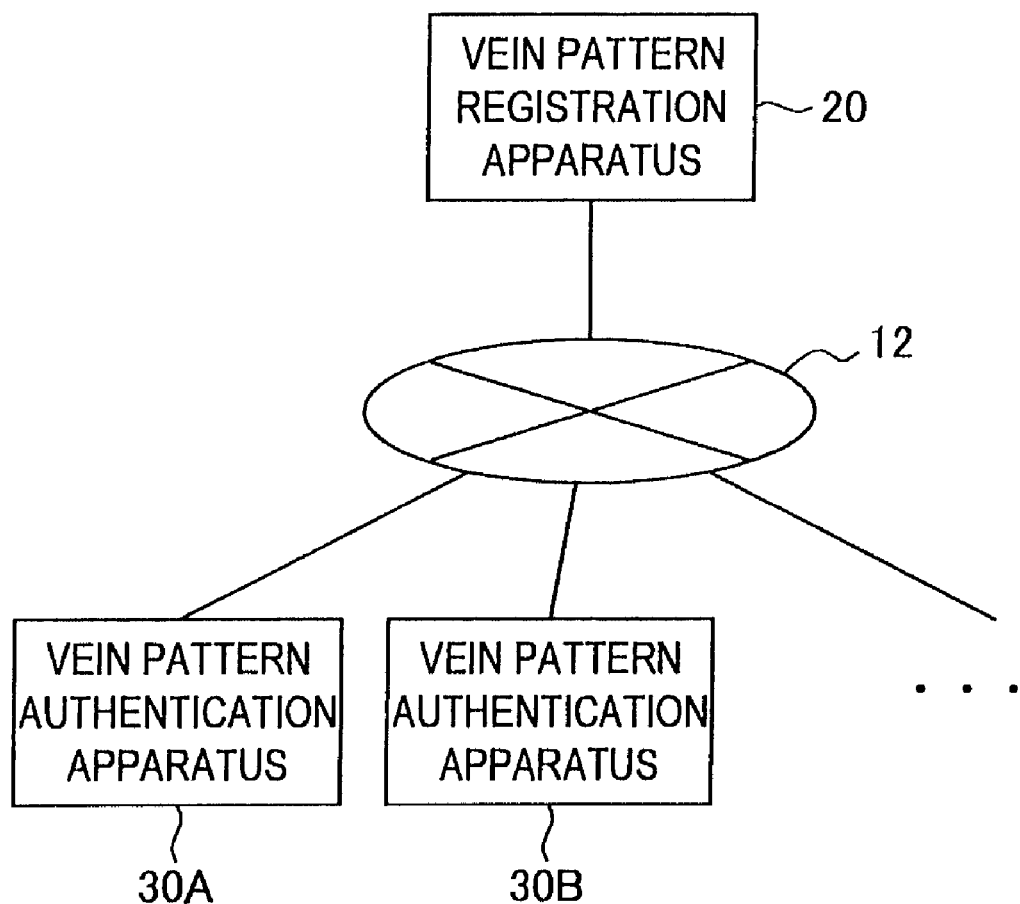
FIG. 5 is an explanatory diagram illustrating a vein pattern management system according to an embodiment of the present invention.

Next, referring to FIG. 5, a vein pattern management system 10 according to this embodiment will be described in detail. FIG. 5 is an explanatory diagram illustrating the vein pattern management system 10 according to this embodiment.

As shown in FIG. 5, the vein pattern management system 10 include, for example, a vein pattern registration apparatus 20, and a plurality of vein pattern authentication apparatuses 30A, 30B, . . . , which are connected to the vein pattern registration apparatus 20 via a network 12.

The network 12 is a communication line network that connects the vein pattern registration apparatus 20 and a vein pattern authentication apparatus 30 such that they can communicate in either unidirection or bidirection. The network 12 may include, for example, public network, such as Internet, telephone network, satellite communication network, or multicasting network, private network, such as Wide Area Network (WAN), Local Area Network (LAN), Internet Protocol-Virtual Private Network (IP-VPN), Ethernet (registered trademark), or wireless LAN, and the like, and is limited neither to wired network nor wireless network.

The vein pattern registration apparatus 20 is operable to radiate light of a predetermined wavelength to a body surface of an individual desiring to register his/her vein pattern, capture an image of the body surface, extract a vein pattern from the captured image data, and register the extracted vein pattern as personal identity information. The vein pattern registration apparatus 20 is also operable to determine presence of a pseudo-vein pattern intentionally formed on the body surface and determine whether the extracted vein pattern should be registered or not. In addition, the vein pattern registration apparatus 20 may disclose registered vein patterns, which have been registered as the personal identity information, as required by the vein pattern authentication apparatus 30 to be described later.

The vein pattern authentication apparatuses 30A and 30B are operable to radiate light of the predetermined wavelength to a body surface of an individual desiring to register his/her vein pattern, capture an image of the body surface, extract a vein pattern from the captured image data, and compare the extracted vein pattern with already registered vein patterns to authenticate the individual. The vein pattern authentication apparatus 30 is also operable to determine presence of a pseudo-vein pattern intentionally formed on the body surface and determine whether the extracted vein pattern should be authenticated or not. In addition, the vein pattern authentication apparatuses 30A and 30B may request the vein pattern registration apparatus 20 to disclose the already registered vein patterns.

It is noted that the vein pattern registration apparatus 20 and the vein pattern authentication apparatus 30A and 30B may be connected via the network 12 as shown in the figures, or may be directly connected via a Universal Serial Bus (USB) port, an IEEE 1394 port, such as an i.LINK, a Small Computer System Interface (SCSI) port, a RS-232C port, or the like, not via the network 12.

Although, in FIG. 5, there is only one vein pattern registration apparatus 20 connected to a network 12, this embodiment is not intended to be limited to a configuration as described above, but may allow a plurality of vein pattern registration apparatuses 20 to be connected on the network 12. Similarly, in FIG. 5, there are only two vein pattern authentication apparatuses 30 which are connected to the network 12, and a plurality of vein pattern authentication apparatuses 30 may be connected on the network 12.

(Configuration of Vein Pattern Registration Apparatus 20)

Figure 6:
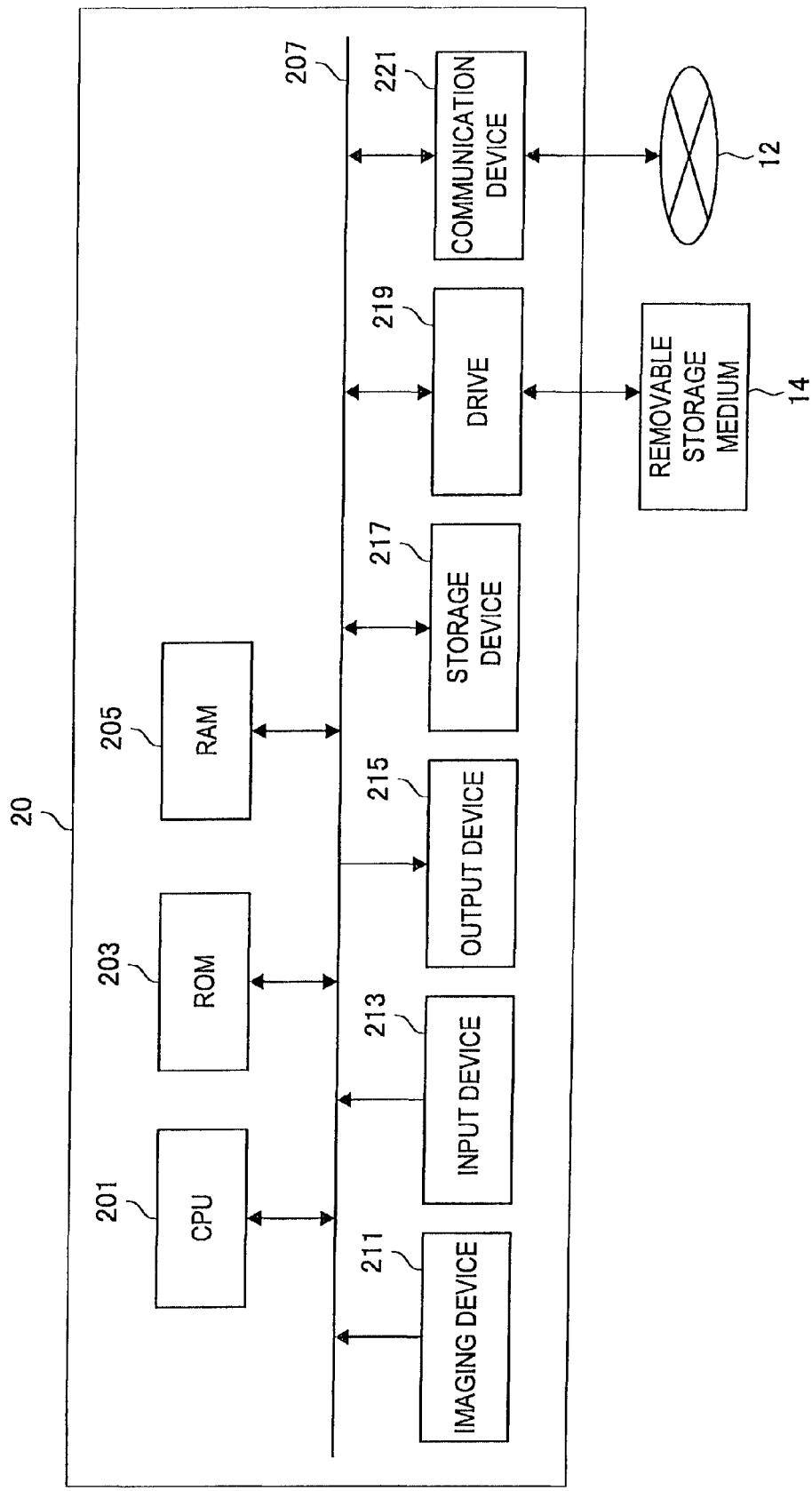
FIG. 6 is a block diagram illustrating a hardware configuration of a vein pattern registration apparatus according to the embodiment.

Referring to FIG. 6, a hardware configuration of a vein pattern registration apparatus 20 according to this embodiment will be described in detail. FIG. 6 is a block diagram illustrating the hardware configuration of the vein pattern registration apparatus 20 according to this embodiment.

As shown in FIG. 6, the vein pattern registration apparatus 20 mainly includes Central Processing Unit (CPU) 201, Read Only Memory (ROM) 203, Random Access Memory (RAM) 205, a bus 207, an imaging device 211, an input device 213, an output device 215, a storage device 217, a drive 219, and a communication device 221.

CPU 201 serves as a computing device and a controller for controlling all or a part of operations in the vein pattern registration apparatus 20 in accordance with various programs recorded in ROM 203, RAM 205, the storage device 217 or a removable recording medium 14. ROM 203 stores programs, operational parameters, and the like used by CPU 201. RAM 205 temporarily stores a program for use in execution by CPU 201, parameters that change appropriately in the execution of the program, and the like. CPU, ROM, and RAM are connected with each other via the bus 207 formed by an internal bus, such as a CPU bus.

The imaging device 211 is a device that captures an image of a body surface to generate image data under control of CPU 201. The imaging device 211 includes, for example, a radiation device for radiating light of a predetermined wavelength and a focusing device, such as an optical lens, for focusing light transmitting through the body surface. The radiation device includes a light source emitting the light of the predetermined wavelength and radiates the light of the predetermined wavelength based on a control signal from CPU 201. The focusing device collects the light radiated from the radiation device and generates the image data.

The input device 213 includes, for example, an operation means, such as mouse, a keyboard, a touch panel, a button, a switch, and a lever, which is operated by a user, and an audio input means, such as a microphone and a headset. In addition, the input device 213 may be, for example, a remote control means (what is called remote controller) using infrared radiation or other radio waves, or may be an external connection device, such as a mobile telephone and PDA, adapted to the operation of the vein pattern registration apparatus 20. Furthermore, the input device 213 may include, for example, an input control circuit or the like, for generating an input signal based on information input by the user using the above-mentioned operation means and audio input means and outputting the input signal to CPU 201. The user of the vein pattern registration apparatus 20 can input various data and instruct a processing operation to the vein pattern registration apparatus 20 by operating the input device 213.

The output device 215 includes, for example, a display device, such as a Cathode Ray Tube (CRT) display device, a Liquid Crystal Display (LCD) device, a Plasma Display Panel (PDP) device, an Electro-Luminescence (EL) display device and a lamp, an audio output device, such as a speaker and head phones, a printer, a mobile phone, a facsimile machine, and the like, which are capable of visually or audibly communicating acquired information to the user.

The storage device 217 is a data storing device, which is configured as an example of a storage unit of the vein pattern registration apparatus 20 according to this embodiment, and includes, for example, a magnetic storage device, such as a hard disk drive (HDD), a semiconductor storage device, an optical storage device, a magnetic optical storage device, or the like. The storage device 217 stores a wide variety of data, such as programs executed by CPU 201, various data, and various types of data acquired from an outside.

The drive 219 is a reader/writer for a storing medium and may be embedded in or attached externally to the vein pattern registration apparatus 20. The drive 219 reads out information recorded in the removable recording medium 14, such as an attached magnetic disk, optical disk, magnetic optical disk, or semiconductor memory, and outputs the information to RAM 205. In addition, the drive 219 is capable of writing recordings to the removable recording medium 14, such as the attached magnetic disk, optical disk, magnetic optical disk, or semiconductor memory. The removable recording medium 14 includes, for example, a DVD medium, a HD-DVD medium, a Blu-ray medium, CompactFlash (CF) (registered trademark), a memory stick, a Secure Digital (SD) memory card, or the like. In addition, the removable recording medium 14 may be, for example, in a form of an Integrated Circuit (IC) card equipped with a non-contact IC chip, an electronic device, or the like.

The communication device 221 is a communication interface, which include, for example, a communication device for connecting to a communication network 12. The communication device 221 is made in a form of a communication card for use in wired or wireless Local Area Network (LAN), Bluetooth, or Wireless USB (WUSB), a router for use in optical communication, a router for use in Asymmetric Digital Subscriber Line (ADSL), a modem for use in various communication environments, or the like. This communication device 221 is capable of sending/receiving signals and the like to/from other vein pattern registration devices 20 and other vein pattern authentication devices 30. In addition, the network 12 connected to the communication device 221 is formed by networks and the like connected via wired or wireless connection, and may be configured, for example, as Internet, home LAN, infrared communication, satellite communication, or the like.

With a configuration as described above, the vein pattern registration apparatus 20 can radiate light of a predetermined wavelength to a body surface of an individual desiring to register his/her vein pattern, capture an image of the body surface, extract a vein pattern from the captured image data, and register the extracted vein pattern as personal identity information. In addition, the vein pattern registration apparatus 20 can send/receive data to/from the vein pattern authentication apparatus 30 directly connected to the vein pattern registration apparatus 20 or the vein pattern authentication apparatus 30 connected to the network 12, and retrieve information stored in the vein pattern registration apparatus 20 using the removable recording medium 14.

An example of a possible hardware configuration for implementing functions of vein pattern registration apparatus 20 according to this embodiment has been described above. Each of the above components may be configured using a general purpose member, or may be configured with a dedicated hardware for a function of each component. Thus, the hardware configuration used herein can be appropriately modified depending on state of the art at the time of implementing this embodiment.

A description of a hardware configuration of the vein pattern authentication apparatus 30 is omitted, since the hardware configuration of the vein pattern authentication apparatus 30 is substantially identical to that of the vein pattern registration apparatus 20.

Figure 7:
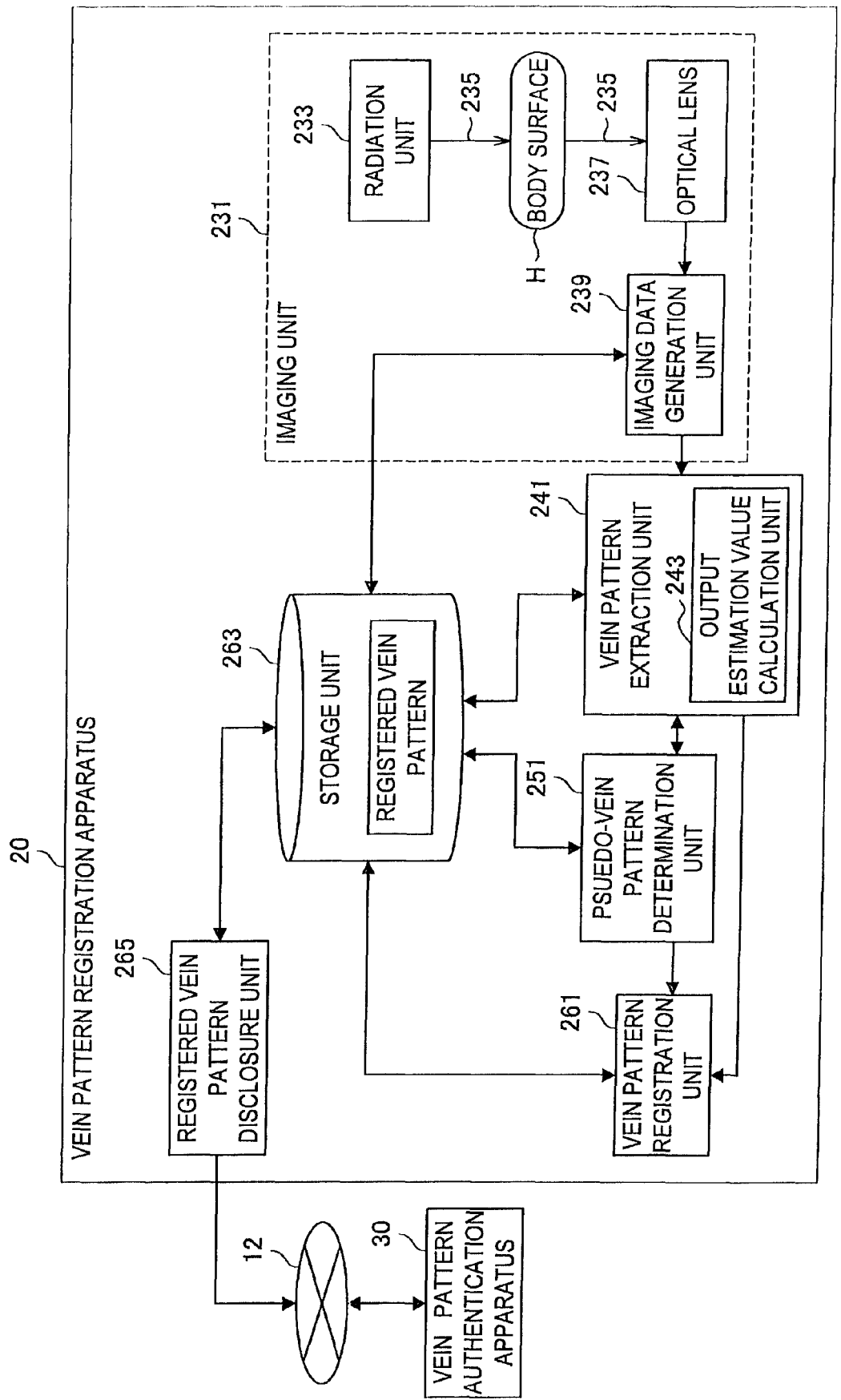
FIG. 7 is a block diagram illustrating a configuration of the vein pattern registration apparatus according to the embodiment.

Next, referring to FIG. 7, a configuration of a vein pattern registration apparatus 20 according to this embodiment will be described in detail. FIG. 7 is a block diagram illustrating the configuration of the vein pattern registration apparatus 20 according to this embodiment.

As shown in FIG. 7, the vein pattern registration apparatus 20 according to this embodiment includes, for example, an imaging unit 231, a vein pattern extraction unit 241, a pseudo-vein pattern determination unit 251, a vein pattern registration unit 261, a storage unit 263, and a registered vein pattern disclosure unit 265.

The imaging unit 231 captures an image of a body surface H of an individual desiring to register his/her vein pattern and generates imaging data. The imaging unit 231 includes, for example, a radiation unit 233 radiating light of a predetermined wavelength, an optical lens 237 focusing light transmitting through the body surface H, and an imaging data generation unit 239 generating imaging data based on the focused light.

The radiation unit 233 includes a light source, such as a halogen lamp and a light emitting diode, which radiates near-infrared light to the body surface H and radiates near-infrared light 235 having a wavelength of about 600 nm to about 1,300 nm.

The optical lens 237 focuses the near-infrared light 235 transmitting through the body surface H, such as a finger surface, and forms an image on the imaging data generation unit 239. The optical lens 237 according to this embodiment is capable of focusing the near-infrared light 235 by changing a magnification to a predetermined magnification. In order to focus the near-infrared light 235 to form an image at various magnifications, the optical lens 237 according to this embodiment may include multiple optical lenses having different focal lengths, respectively, or may include a multifocal lens having a variable focal length.

The imaging data generation unit 239 generates near-infrared light imaging data of various magnifications based on transmitted light of the near-infrared light 235, which has been focused by the optical lens 237. The imaging data generation unit 239 includes, for example, a Charge Coupled Device (CCD) image sensor, a Complementary-Metal Oxide Semiconductor (C-MOS) image sensor, or the like and outputs the near-infrared light imaging data to the vein pattern extraction unit 241 to be described later. In addition, the imaging data generation unit 239 may store the generated near-infrared light imaging data in the storage unit 273 to be described later. In storing in the storage unit 273, date of capture or time of capture may be associated to the generated near-infrared light imaging data. Furthermore, the generated near-infrared light imaging data may be in the form of a Red-Green-Blue (RGB) signal or may be image data of other colors, gray scale image data, or the like.

The vein pattern extraction unit 241 includes, for example, a function of performing a pre-process for vein pattern extraction on the near-infrared light imaging data transmitted from the imaging data generation unit 239, a function of extracting a vein pattern, and a function of performing a post-process for the vein pattern extraction.

The pre-process for the vein pattern extraction includes, for example, a process for detecting a contour of a finger from near-infrared light imaging data and discriminating where the finger is located in the near-infrared light imaging data, a process for rotating the near-infrared light imaging data using the detected contour of the finger and correcting an angle of the near-infrared light imaging data (an angle of captured image), and the like.

In addition, the vein pattern extraction may be achieved by applying a differential filter to the near-infrared light imaging data, which has been subject to detecting the contour or correcting the angle. The differential filter is a filter that outputs a high value as an output value for an image of interest and its surrounding pixels at a portion where differences between the pixel of interest and its surrounding pixels, respectively, are large. In other words, the differential filter as used herein refers to a filter that enhances a line or an edge in an image by an operation using differences in gray level values between a pixel of interest and its surroundings.

In general, performing a filtering process on image data u(x, y) with a variable, which is a lattice point (x, y) on a two-dimensional plane, using a filter h(x, y) results in image data v(x, y), as shown in the following Equation 2. In the following Equation 2, * denotes convolution.

$$v(x, y) = u(x, y) * h(x, y) \qquad (2)$$
$$= \sum_{m_1}\sum_{m_2} h(m_1, m_2)u(x-m_1, y-m_2)$$
$$= \sum_{m_1}\sum_{m_2} u(m_1, m_2)h(x-m_1, y-m_2)$$

In the vein pattern extraction according to this embodiment, a derivative filter, such as a first order spatial derivative filter or a second order spatial derivative filter may be used as the above-mentioned differential filter. The first order spatial derivative filter refers to a filter that, for a pixel of interest, calculates a difference in gray scale levels between the pixel of interest and its horizontally adjacent pixel or its vertically adjacent pixel, and the second order spatial derivative filter refers to a filter that extracts a portion having an increased variation in differences in gray scale values for a pixel of interest.

For example, the following Laplacian of Gaussian (Log) filter can be used as the above-mentioned second order spatial derivative filter. The Log filter (Equation 4) can be written as a second order derivative of a Gaussian filter (Equation 3), which is a smoothing filter using a Gauss function. In the following Equation 3, σ represents a standard deviation of the Gauss function, in other words, a variable representing a degree of smoothing for the Gaussian filter. Furthermore, σ in the following Equation 4 is also a parameter, which represent a standard deviation of the Gauss function, as is the case with Equation 3, and changing a value of σ can cause an output value to change in case of performing a Log filtering process.

$$h_{gauss}(x, y) = \frac{1}{2\pi\sigma^2}\exp\left\{-\frac{(x^2+y^2)}{2\sigma^2}\right\} \qquad (3)$$

$$h_{Log}(x, y) = \nabla^2 \cdot h_{gauss}(x, y) \qquad (4)$$
$$= \left(\frac{\partial^2}{\partial x^2} + \frac{\partial^2}{\partial y^2}\right) h_{gauss}$$
$$= \frac{(x^2+y^2-2\sigma^2)}{2\pi\sigma^6}\exp\left\{-\frac{(x^2+y^2)}{2\sigma^2}\right\}$$

Also the above-described post-process for the vein pattern extraction may include, for example, a threshold process performed on image data, which has been subject to a differential filter, a binarization process, a thinning process, and the like. After having passed through the post-process, a skeleton of the vein pattern can be extracted.

The vein pattern extraction unit 241 transmits the vein pattern or the skeleton thus extracted to the output estimation value calculation unit 243 to be described later. The vein pattern extraction unit 241 may also store the extracted vein pattern or skeleton in the storage unit 273 to be described later. It is noted that the vein pattern extraction unit 241 may store a parameter, intermediate results during the processes, and the like, which have been generated to perform each of the above-mentioned processes, in the storage unit 273.

Furthermore, the vein pattern extraction unit 241 includes an output estimation value calculation unit 243 for calculating an output estimation value indicating a ratio of a sum of output values, which are more than a predetermined upper output value, among acquired output values of the differential filter relative to a total sum of the acquired output values of the differential filter. In this instance the output estimation value means a value defined as Equation 5 as follows, and is used in determining whether a pseudo-vein pattern is present or not.

$$r(v^{thr}) = \frac{S(v^{thr})}{S(0)} \qquad (5)$$

In Equation 5, $v^{thr}$ represents an upper output value of the differential filter, $S(v^{thr})$ represents a sum of output values more than the upper output value $v^{thr}$ of the differential filter, and $r(v^{thr})$ represents an output estimation value. In addition, S(0) indicates a sum of the output values of the differential filter when the upper output value of the differential filter satisfies $v^{thr}=0$ and also indicates a simple total sum of the output values of the differential filter.

It is noted that the above-mentioned $v^{thr}$ is a value which has been previously set based on an output value distribution of the differential filter calculated from a prior determination test or the like using multiple estimation data.

The output estimation value calculation unit 243 may transmit the output estimation value calculated according to Equation 5, for example, to the pseudo-vein pattern determination unit 251 to be described later. In addition, the output estimation value calculation unit 243 may store the calculated output estimation value in the storage unit 263.

The pseudo-vein pattern determination unit 251 determines presence of a pseudo-vein pattern intentionally formed on a part of the body surface H based on the output estimation value transmitted from the output estimation value calculation unit 243 of the vein pattern extraction unit 241. In particular, the pseudo-vein pattern determination unit 251 determines the presence of the pseudo-vein pattern by comparing the output estimation value transmitted from the output estimation value calculation unit 243 with a predetermined threshold value. The threshold value may be, for example, a value which has been previously calculated from a prior determination test or the like using multiple estimation data or a value unique to a particular individual.

In particular, the pseudo-vein pattern determination unit 251 determines that no pseudo-vein patterns have been formed on the part of the body surface H when the output estimation value transmitted from the output estimation value calculation unit 243 is equal to or more than the predetermined threshold value, and determines that a pseudo-vein pattern has been formed on the part of the body surface H when the output estimation value is less than the predetermined threshold value.

The pseudo-vein pattern determination unit 251 transmits a determination result to the vein pattern registration unit 261. The pseudo-vein pattern determination unit 251 may also store the determination result in the storage unit 263. Furthermore, in storing in the storage unit 263, the vein pattern that has been subject to the determination and the determination result may be stored in association with each other.

The vein pattern registration unit 261 registers a generated near-infrared light vein pattern as a template based on the determination result transmitted from the pseudo-vein pattern determination unit 251. In particular, when the determination result is transmitted from the pseudo-vein pattern determination unit 251, indicating that there is not presence of a pseudo-vein pattern, the vein pattern registration unit 261 stores the near-infrared light vein pattern transmitted from the vein pattern extraction unit 241 as a registered vein pattern in the storage unit 263. To the contrary, when the determination result is transmitted from the pseudo-vein pattern determination unit 251, indicating that there is presence of a pseudo-vein pattern, the vein pattern registration unit 261 does not register the extracted near-infrared light vein pattern and finishes a registration process. In registration of the registered vein pattern, not only the near-infrared light vein pattern is stored, but also other data for identifying an individual (for example, fingerprint data, face image data, iris data, voice-print data, or the like) having the vein pattern may be stored in association with the near-infrared light vein pattern. Moreover, the registered vein pattern to be registered as the template may contain, for example, header information in conformity to a standard, such as a Common Biometric Exchange File Format (CBEFF) framework.

The storage unit 263 stores a registered vein pattern, which is requested to be registered from the vein pattern registration unit 261, or other data associated to the registered vein pattern. In addition to these data, imaging data generated by the imaging data generation unit 239, a vein pattern extracted by the vein pattern extraction unit 241, or the like may also be stored. Furthermore, in addition to these data, the vein pattern registration apparatus 20 can cause various parameters, intermediate results, and the like, which are needed to be stored in performing some processes, or a variety of databases and the like to be appropriately stored. This storing unit 273 can be freely read from/written to by the imaging unit 231, vein pattern extraction unit 241, pseudo-vein pattern determination unit 251, vein pattern registration unit 261, and the like.

The registered vein pattern disclosure unit 265 may disclose a registered vein pattern stored in the storage unit 263, for example, as required by the vein pattern authentication apparatus 30 connected to the vein pattern registration apparatus 20.

It is noted that the vein pattern registration apparatus 20 according to this embodiment may be implemented in various apparatuses, such as an information processing apparatus including a computer or a server, a mobile terminal or a personal digital assistant (PDA) including a mobile telephone or PHS, an automated teller machine (ATM), an entrance and exit control apparatus, and the like, for example.

Although in the above description, the registered vein pattern to be registered as the template has been described in a case of storing the pattern within the vein pattern registration apparatus 20, the registered vein pattern may be stored in a recording medium, such as DVD media, HD-DVD media, Blu-ray media, CompactFlash (registered trademark), memory stick, SD memory card, or the like, an IC card equipped with a non-contact IC chip, an electronic equipment, and the like.

An example of functions of vein pattern registration apparatus 20 according to this embodiment has been described above. Each of the above components may be configured using a general purpose member or circuit, or may be configured with a dedicated hardware for a function of each component. In addition, a function of each component may be achieved by only CPU or the like. Thus, a configuration used herein can be appropriately modified depending on state of the art at the time of implementing this embodiment.

(Configuration of Vein Pattern Authentication Apparatus 30)

Figure 8:
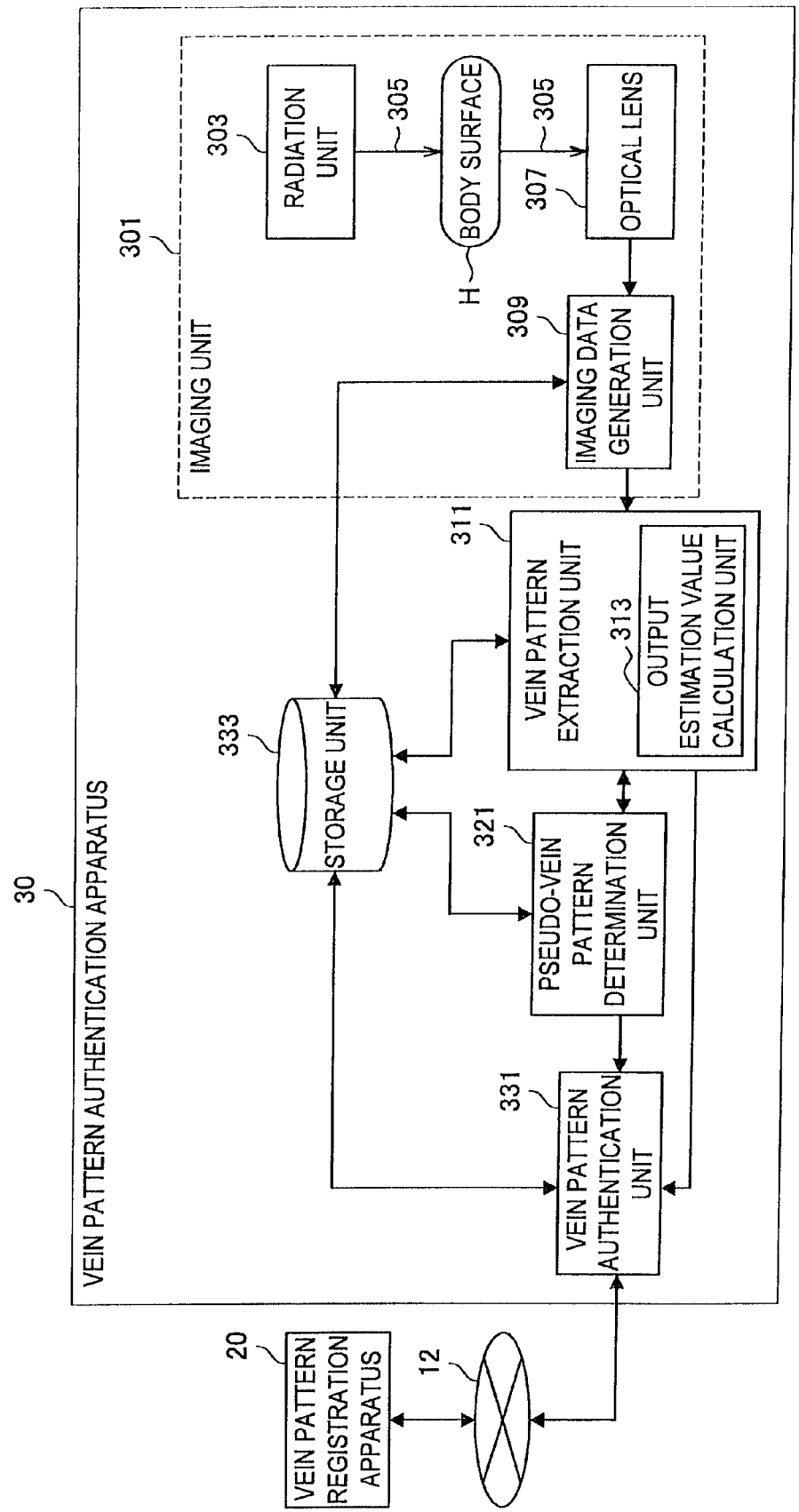
FIG. 8 is a block diagram illustrating a configuration of a vein pattern authentication apparatus according to the embodiment.

Next, referring to FIG. 8, a configuration of a vein pattern authentication apparatus 30 according to this embodiment will be described in detail. FIG. 8 is a block diagram illustrating the configuration of the vein pattern authentication apparatus 30 according to this embodiment.

As shown in FIG. 8, the vein pattern authentication apparatus 30 according to this embodiment includes, for example, an imaging unit 301, a vein pattern extraction unit 311, a pseudo-vein pattern determination unit 321, a vein pattern authentication unit 331, and a storage unit 333.

The imaging unit 301 captures an image of a body surface H of an individual desiring to register his/her vein pattern and generates imaging data. The imaging unit 301 includes, for example, a radiation unit 303 radiating light of a predetermined wavelength, an optical lens 307 focusing light transmitting through the body surface H, and an imaging data generation unit 309 generating imaging data based on the focused light.

The radiation unit 303 includes a light source, such as a halogen lamp and a light emitting diode, which radiates near-infrared light to the body surface H and radiates near-infrared light 305 having a wavelength of about 600 nm to about 1,300 nm.

The optical lens 307 focuses the near-infrared light 305 transmitting through the body surface H, such as a finger surface, and forms an image on the imaging data generation unit 309.

The imaging data generation unit 309 generates near-infrared light imaging data of various magnifications based on transmitted light of the near-infrared light 305, which has been focused by the optical lens 307. The imaging data generation unit 309 includes, for example, a CCD image sensor, a C-MOS image sensor, or the like and outputs the near-infrared light imaging data to the vein pattern extraction unit 311 to be described later. In addition, the imaging data generation unit 309 may store the generated near-infrared light imaging data in the storage unit 333 to be described later. In storing in the storage unit 333, date of capture or time of capture may be associated to the generated near-infrared light imaging data. Furthermore, the generated near-infrared light imaging data may be in the form of a Red-Green-Blue (RGB) signal or may be image data of other colors, gray scale image data, or the like.

The vein pattern extraction unit 311 includes, for example, a function of performing a pre-process for vein pattern extraction on the near-infrared light imaging data transmitted from the imaging data generation unit 309, a function of extracting a vein pattern, and a function of performing a post-process for the vein pattern extraction.

The pre-process for the vein pattern extraction includes, for example, a process for detecting a contour of a finger from near-infrared light imaging data and discriminating where the finger is located in the near-infrared light imaging data, a process for rotating the near-infrared light imaging data using the detected contour of the finger and correcting an angle of the near-infrared light imaging data (an angle of captured image), and the like.

In addition, the vein pattern extraction may be achieved by applying a differential filter to the near-infrared light imaging data, which has been subject to detecting the contour or correcting the angle. The differential filter is a filter that outputs a high value as an output value for a pixel of interest and its surrounding pixels at a portion where differences between the pixel of interest and its surrounding pixels, respectively, are large. In other words, the differential filter as used herein refers to a filter that enhances a line or an edge in an image by an operation using differences in gray level values between a pixel of interest and its surroundings.

In general, performing a filtering process on image data $u(x, y)$ with a variable, which is a lattice point $(x, y)$ on a two-dimensional plane, using a filter $h(x, y)$ results in image data $v(x, y)$, as shown in the following Equation 6. In the following Equation 6, * denotes convolution.

$$v(x, y) = u(x, y) * h(x, y) \quad (6)$$
$$= \sum_{m_1} \sum_{m_2} h(m_1, m_2) u(x - m_1, y - m_2)$$
$$= \sum_{m_1} \sum_{m_2} u(m_1, m_2) h(x - m_1, y - m_2)$$

In the vein pattern extraction according to this embodiment, a derivative filter, such as a first order spatial derivative filter or a second order spatial derivative filter may be used as the above-mentioned differential filter. The first order spatial derivative filter refers to a filter that, for a pixel of interest, calculates a difference in gray scale levels between the pixel of interest and its horizontally adjacent pixel or its vertically adjacent pixel, and the second order spatial derivative filter refers to a filter that extracts a portion having an increased variation in differences in gray scale values for a pixel of interest.

For example, the following Laplacian of Gaussian (Log) filter can be used as the above-mentioned second order spatial derivative filter. The Log filter (Equation 8) can be written as a second order derivative of a Gaussian filter (Equation 7), which is a smoothing filter using a Gauss function. In the following Equation 7, σ represents a standard deviation of the Gauss function, and in other words a variable representing a degree of smoothing for the Gaussian filter. Furthermore, σ in the following Equation 8 is also a parameter, which represent a standard deviation of the Gauss function, as is the case with Equation 7, and changing a value of σ can cause an output value to change in case of performing a Log filtering process.

$$h_{gauss}(x, y) = \frac{1}{2\pi\sigma^2} \exp\left\{-\frac{(x^2 + y^2)}{2\sigma^2}\right\} \quad (7)$$

$$h_{Log}(x, y) = \nabla^2 \cdot h_{gauss}(x, y) \quad (8)$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6} \exp\left\{-\frac{(x^2 + y^2)}{2\sigma^2}\right\}$$

Also, the above-described post-process for the vein pattern extraction may include, for example, a threshold process performed on image data, which has been subject to a differential filter, a binarization process, a thinning process, and the like. After having passed through the post-process, a skeleton of the vein pattern can be extracted.

The vein pattern extraction unit 311 transmits the vein pattern or the skeleton thus extracted to the output estimation value calculation unit 313 to be described later. The vein pattern extraction unit 311 may also store the extracted vein pattern or skeleton in the storage unit 333 to be described later. It is noted that the vein pattern extraction unit 311 may store a parameter, intermediate results during the processes, and the like, which have been generated to perform each of the above-mentioned processes, in the storage unit 333.

In addition, the vein pattern extraction unit 311 further includes an output estimation value calculation unit 313 for calculating an output estimation value indicating a ratio of a sum of output values, which are more than a predetermined upper output value, among acquired output values of the differential filter relative to a total sum of the acquired output values of the differential filter. In this instance the output estimation value means a value defined as Equation 9 as follows, and is used in determining whether a pseudo-vein pattern is present or not.

$$r(v^{thr}) = \frac{S(v^{thr})}{S(0)} \quad (9)$$

In Equation 9, $v^{thr}$ represents an upper output value of the differential filter, $S(v^{thr})$ represents a sum of output values more than the upper output value $v^{thr}$ of the differential filter, and $r(v^{thr})$ represents an output estimation value. In addition, $S(0)$ indicates a sum of the output values of the differential filter when the upper output value of the differential filter satisfies $v^{thr}=0$ and also indicates a simple total sum of the output values of the differential filter.

It is noted that the above-mentioned $v^{thr}$ is a value which has been previously set based on an output value distribution of the differential filter calculated from a prior determination test or the like using multiple estimation data.

The output estimation value calculation unit 313 may transmit the output estimation value calculated according to Equation 9, for example, to the pseudo-vein pattern determination unit 321 to be described later. In addition, the output estimation value calculation unit 313 may store the calculated output estimation value in the storage unit 333.

The pseudo-vein pattern determination unit 321 determines presence of a pseudo-vein pattern intentionally formed on a part of the body surface H based on the output estimation value transmitted from the output estimation value calculation unit 313 of the vein pattern extraction unit 311. In particular, the pseudo-vein pattern determination unit 321 determines the presence of the pseudo-vein pattern by comparing the output estimation value transmitted from the output estimation value calculation unit 313 with a predetermined threshold value. The threshold value may be, for example, a value which has been previously calculated from a prior determination test or the like using multiple estimation data or a value unique to a particular individual.

In particular, the pseudo-vein pattern determination unit 321 determines that no pseudo-vein patterns have been formed on the part of the body surface H when the output estimation value transmitted from the output estimation value calculation unit 313 is equal to or more than the predetermined threshold value, and determines that a pseudo-vein pattern has been formed on the part of the body surface H when the output estimation value is less than the predetermined threshold value.

The pseudo-vein pattern determination unit 321 transmits a determination result to the vein pattern authentication unit 331. The pseudo-vein pattern determination unit 321 may also store the determination result in the storage unit 333. Furthermore, in storing in the storage unit 333, the vein pattern that has been subject to the determination and the determination result may be stored in association with each other.

The vein pattern authentication unit 331 performs authentication of a generated near-infrared light vein pattern based on the determination result transmitted from the pseudo-vein pattern determination unit 321. In particular, when the determination result is transmitted from the pseudo-vein pattern determination unit 321, indicating that there is not presence of a pseudo-vein pattern, for example, the vein pattern authentication unit 331 request the vein pattern registration apparatus 20 to disclose a registered vein pattern and compares the registered vein pattern acquired from the vein pattern registration apparatus 20 with the near-infrared light vein pattern transmitted from the vein pattern extraction unit 311. A process of comparing the registered vein pattern with the near-infrared light vein pattern can be achieved, for example, by calculating a correlation coefficient to be described later and performing comparison based on the calculated correlation coefficient. The vein pattern authentication unit 331 authenticates the near-infrared light vein pattern when a comparison result indicates that the registered vein pattern and the near-infrared light vein pattern are similar with each other and does not authenticate the near-infrared light vein pattern when they are not similar with each other.

The correlation coefficient is defined in the following Equation 10, is a statistical measure indicating similarity between two pieces of data: $x=\{x_i\}$ and $y=\{y_i\}$, and has a real value from −1 to 1. When the correlation coefficient has a value close to 1, it indicates that the two pieces of the data are similar with each other, and when the correlation coefficient has a value close to 0, it indicates that the two pieces of the data are not similar with each other. In addition, when the correlation coefficient has a value close to −1, it indicates a case where the two pieces of the data have inverted signs, respectively.

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad (10)$$

$\bar{x}$: Average of Data x
$\bar{y}$: Average of Data y

To the contrary, when the determination result is transmitted from the pseudo-vein pattern determination unit 331, indicating that there is presence of a pseudo-vein pattern, the vein pattern authentication unit 341 does not perform and finishes an authentication process of the extracted near-infrared light vein pattern.

The storage unit 333 is capable of storing imaging data generated by the imaging data generation unit 309, the vein pattern extracted by the vein pattern extraction unit 311, or the like. Furthermore, in addition to these data, the vein pattern authentication apparatus 30 can cause various parameters, intermediate results, and the like, which are needed to be stored in performing some processes, or a variety of databases and the like to be appropriately stored. This storing unit 333 can be freely read from/written to by the imaging unit 301, vein pattern extraction unit 311, pseudo-vein pattern determination unit 321, vein pattern authentication unit 331, and the like.

The vein pattern authentication apparatus 30 according to this embodiment may be implemented in various apparatuses, such as an information processing apparatus including a computer or a server, a mobile terminal or a personal digital assistant (PDA) including a mobile telephone or PHS, an automated teller machine (ATM), an entrance and exit control apparatus, and the like, for example.

Although in the above description, the registered vein pattern is supposed to be acquired from the vein pattern registration apparatus 20, the authentication may be performed based on the registered vein pattern, which has been stored in a recording medium, such as DVD media, HD-DVD media, Blu-ray media, CompactFlash (registered trademark), memory stick, SD memory card, or the like, an IC card equipped with a non-contact IC chip, an electronic equipment, and the like. Furthermore, the registered vein pattern may be stored in the vein pattern authentication apparatus 30.

An example of functions of vein pattern authentication apparatus 30 according to this embodiment has been described above. Each of above components may be configured using a general purpose member or circuit, or may be configured with a dedicated hardware for a function of each component. In addition, a function of each component may be achieved by only CPU or the like. Thus, a configuration used herein can be appropriately modified depending on state of the art at the time of implementing this embodiment.

(Registration Method of Vein Pattern)

Next, referring to FIG. 9, a method for registering a vein pattern according to this embodiment will be described in detail. FIG. 9 is a flowchart illustrating a method for discriminating pseudo-vein patterns according to this embodiment.

The method for registering a vein pattern according to this embodiment is characterized in that presence of a pseudo-vein pattern is determined based on output values of a differential filter in taking account of a difference in an output value distribution of the differential filter between presence and absence of a pseudo-vein pattern.

First, an imaging unit 231 captures an image of a part of a body surface (for example, a finger surface) with near-infrared light 235 and an imaging data generation unit 239 in the imaging unit 231 generates near-infrared light imaging data (step S101). The imaging data generation unit 239 stores the generated near-infrared light imaging data in a storage unit 263, for example, in association with date of capture or time of capture, and transmits the generated near-infrared light imaging data to a vein pattern extraction unit 241.

The vein pattern extraction unit 241, to which the near-infrared light imaging data transmitted, performs a pre-process for skeleton extraction of a vein pattern on the near-infrared light imaging data, in which the pre-process includes a process for detecting a contour of a finger and discriminating a position of the finger, or a process for rotating the near-infrared light imaging data and correcting an angle of the near-infrared light imaging data (step S103).

Once the pre-process for the skeleton extraction has finished, the vein pattern extraction unit 241 then calculates a Log filter output by applying a Log filter process, which is a kind of differential filters, to the near-infrared light imaging data, which has been subject to the pre-process (step S105), and presumes the Log filter output as a near-infrared light vein pattern. After calculating an output value of the Log filter, the vein pattern extraction unit 241 stores the calculated output value of the Log filter (near-infrared light vein pattern) in the storage unit 263.

An output estimation value calculation unit 243 in the vein pattern extraction unit 241 calculates an output estimation value based on the calculated output value of the Log filter after calculating the output value of the Log filter (step S107). In calculation of the estimated output, output values of the Log filter for all pixels constituting the near-infrared light vein pattern (i.e., gray scale values for respective pixels) are compared with a predetermined upper output value, and at the same time, a total sum of the output values of the Log filter for all pixels constituting the near-infrared light vein pattern is calculated. Once a sum of output values of the Log filter, which are more than the upper output value, has been acquired, the output estimation value is calculated according to the above-mentioned Equation 5. Once the output estimation value has been calculated, the output estimation value calculation unit 243 transmits the calculated output estimation value to the pseudo-vein pattern determination unit 251. The output estimation value calculation unit 243 may also store the calculated output estimation value in the storage unit 263.

The pseudo-vein pattern determination unit 251 determines whether a pseudo-vein pattern is present on a part of a body surface (for example, finger surface) based on the output estimation value transmitted from the output estimation value calculation unit 243. Determination of presence is performed by determining whether the calculated output estimation value is equal to or more than a predetermined threshold value or less than the predetermined threshold value (step S109).

On one hand, when the calculated output estimation value is less than the predetermined threshold value, the pseudo-vein pattern determination unit 251 determines that there are no pseudo-vein patterns present on the finger surface that is subject to imaging, and informs the vein pattern extraction unit 241 and a vein pattern registration unit 261 of a determination result. The vein pattern extraction unit 241, to which the determination result has been informed of, performs a post-process, such a threshold process, a binarization process, and a thinning process, on the near-infrared light vein pattern (step S111), and stores the near-infrared light vein pattern subject to the post-process in the storage unit 263 as well as transmits the near-infrared light vein pattern to the vein pattern registration unit 261.

On the other hand, when the calculated output estimation value is equal to or more than the predetermined threshold value, the pseudo-vein pattern determination unit 251 determines that there is a pseudo-vein pattern present on the finger surface that is subject to imaging, and informs the vein pattern registration unit 261 of a determination result.

When the vein pattern registration unit 261 is informed of a signal indicating that there are no pseudo-vein patterns present from the pseudo-vein pattern determination unit 251, the vein pattern registration unit 261 stores the near-infrared light vein pattern subject to the post-process and transmitted from the vein pattern extraction unit 241 as a registered vein pattern in a database (not shown) contained in the storage unit 263. In addition, the registered vein pattern may be associated with ID or other biometrics data of an individual, or the like.

Furthermore, when the vein pattern registration unit 261 is informed of a signal indicating that there is a pseudo-vein pattern present from the pseudo-vein pattern determination unit 251, the vein pattern registration unit 261 does not perform a registration process of the vein pattern and finishes a series of processes.

As described above, in the method for registering a vein pattern according to this embodiment, it is possible to determine presence of a pseudo-vein pattern intentionally formed on a part of a body surface by focusing attention on the magnitude or distribution of output values of a differential filter. Since a method for registering a vein pattern according to this embodiment can determine presence of a pseudo-vein pattern before registering the vein pattern, possibility of storing unnecessary data in a database and the like, in which registered vein patterns are contained, is avoided, and it becomes easy to manage the registered vain patterns.

(Authentication Method of Vein Pattern)

Next, again referring to FIG. 9, a method for authenticating a vein pattern according to this embodiment will be described in detail.

The method for authenticating a vein pattern according to this embodiment is characterized in that presence of a pseudo-vein pattern is determined based on output values of a differential filter in taking account of a difference in an output value distribution of the differential filter between presence and absence of a pseudo-vein pattern.

First, an imaging unit 301 captures an image of a part of a body surface (for example, a finger surface) with near-infrared light 305 and an imaging data generation unit 309 in the imaging unit 301 generates near-infrared light imaging data (step S101). The imaging data generation unit 309 stores the generated near-infrared light imaging data in a storage unit 333, for example, in association with date of capture or time of capture, and transmits the generated near-infrared light imaging data to a vein pattern extraction unit 311.

The vein pattern extraction unit 311, to which the near-infrared light imaging data transmitted, performs a pre-process for skeleton extraction of a vein pattern on the near-infrared light imaging data, in which the pre-process includes a process for detecting a contour of a finger and discriminating a position of the finger, or a process for rotating the near-infrared light imaging data and correcting an angle of the near-infrared light imaging data (step S103).

Once the pre-process for the skeleton extraction has finished, the vein pattern extraction unit 311 then calculates a Log filter output by applying a Log filter process, which is a kind of differential filters, to the near-infrared light imaging data, which has been subject to the pre-process (step S105), and presumes the Log filter output as a near-infrared light vein pattern. After calculating an output value of the Log filter, the vein pattern extraction unit 311 stores the calculated output value of the Log filter (near-infrared light vein pattern) in the storage unit 333.

An output estimation value calculation unit 313 in the vein pattern extraction unit 311 calculates an output estimation value based on the calculated output value of the Log filter after calculating the output value of the Log filter (step S107). In calculation of the estimated output, output values of the Log filter for all pixels constituting the near-infrared light vein pattern (i.e., gray scale values for respective pixels) are compared with a predetermined upper output value, and at the same time, a total sum of the output values of the Log filter for all pixels constituting the near-infrared light vein pattern is calculated. Once a sum of output values of the Log filter, which are equal to or more than the upper output value, has been acquired, the output estimation value is calculated according to the above-mentioned Equation 9. Once the output estimation value has been calculated, the output estimation value calculation unit 243 transmits the calculated output estimation value to a pseudo-vein pattern determination unit 321. The output estimation value calculation unit 313 may also store the calculated output estimation value in the storage unit 333.

The pseudo-vein pattern determination unit 321 determines whether a pseudo-vein pattern is present on a part of a body surface (for example, finger surface) based on the output estimation value transmitted from the output estimation value calculation unit 313. Determination of presence is performed by determining whether the calculated output estimation value is equal to or more than a predetermined threshold value or less than the predetermined threshold value (step S109).

On one hand, when the calculated output estimation value is less than the predetermined threshold value, the pseudo-vein pattern determination unit 321 determines that there are no pseudo-vein patterns present on the finger surface that is subject to imaging, and informs the vein pattern extraction unit 311 and a vein pattern authentication unit 331 of a determination result. The vein pattern extraction unit 331, to which the determination result has been informed of, performs a post-process, such a threshold process, a binarization process, and a thinning process, on the near-infrared light vein pattern (step S111), and stores the near-infrared light vein pattern subject to the post-process in the storage unit 333 as well as transmits the near-infrared light vein pattern to the vein pattern authentication unit 331.

On the other hand, when the calculated output estimation value is equal to or more than the predetermined threshold value, the pseudo-vein pattern determination unit 321 determines that there is a pseudo-vein pattern present on the finger surface that is subject to imaging, and informs the vein pattern authentication unit 331 of a determination result.

When the vein pattern authentication unit 331 is informed of a signal indicating that there are no pseudo-vein patterns present from the pseudo-vein pattern determination unit 321, the vein pattern authentication unit 331 requests the vein pattern registration apparatus 20 to disclose a registered vein pattern. Once the registered vein pattern has been disclosed by a registered vein pattern disclosure unit 265 in the vein pattern registration apparatus 20, the vein pattern authentication unit 331 acquires and compares the disclosed registered vein pattern with the near-infrared light vein pattern, which has been subject to the post-process, transmitted from the vein pattern extraction unit 311. Comparison of the registered vein pattern with the near-infrared light vein pattern is performed, for example, using a method capable of quantitatively calculating similarity, such as above-mentioned correlation coefficient, between image data. The vein pattern authentication unit 331 authenticates the generated near-infrared light vein pattern when the registered vein pattern and the near-infrared light vein pattern are similar with each other, but the vein pattern authentication unit 331 does not authenticate the near-infrared light vein pattern when they are not similar with each other.

Furthermore, when the vein pattern authentication unit 331 is informed of a signal indicating that there is a pseudo-vein pattern present from the pseudo-vein pattern determination unit 331, the vein pattern authentication unit 321 does not perform an authentication process of the vein pattern and finishes a series of processes.

As described above, in the method for authenticating a vein pattern according to this embodiment, it is possible to determine presence of a pseudo-vein pattern intentionally formed on a part of a body surface by focusing attention on the magnitude or distribution of output values of a differential filter. Since a method for authenticating a vein pattern according to this embodiment can determine presence of a pseudo-vein pattern before authenticating the vein pattern, it can previously prevent malicious users from impersonating others by repeating try and error to optimize a pseudo-vein pattern.

(Vein Data Configuration)

Furthermore, according to the present invention, there is provided a vein data configuration including a vein data storage area containing data, which correspond to a vein pattern of an individual and are to be verified with image data acquired by capturing an image of a part of a body surface of a living body with near-infrared light, and an output estimation value storage area containing an evaluated output value, indicating a ratio of a sum of output values, which are more than a predetermined upper output value, among output values of the differential filter relative to a total sum of the output values of the differential filter for the image data acquired by capturing the image with the near-infrared light.

The vein data storage area is an area containing, for example, a vein pattern that has been registered as a registered vein pattern by the vein pattern registration apparatus 20. The data contained in this vein data storage area are used, for example, by the vein pattern authentication apparatus 30 in authenticating a near-infrared light vein pattern captured.

The output estimation value storage area is an area containing the evaluated output value which indicates the ratio of the sum of the output values more than the predetermined upper output value, among output values of the differential filter relative to the total sum of the output values of the differential filter for the image data acquired by capturing the image with the near-infrared light. The output estimation value contained in this output estimation value storage area are used, for example, by the vein pattern registration apparatus 20 or the vein pattern authentication apparatus 30 in determining presence of a pseudo-vein pattern formed on a body surface.

The above-mentioned vein data configuration further includes a parameter storage area containing a parameter, which changes an output property of a differential filter outputting a high output for an pixel that differs largely from its surrounding pixels, for each pixel constituting the image data acquired by capturing the image with the near-infrared light.

The parameter contained in the parameter storage area is a parameter for a differential filter used, for example, by the vein pattern registration apparatus 20 or the vein pattern authentication apparatus 30 in extracting a vein pattern from imaging data captured with near-infrared light or visible light, and the parameter significantly changes an output value of the differential filter, for example, when the image data acquired by capturing the image with the near-infrared light have a difference greater than that between a value indicating a vein portion and a value indicating a non-vein portion.

The above-mentioned parameter is separately contained for each type of differential filters and makes a pseudo-vein pattern formed on the body surface have a value such that the pseudo-vein pattern can be detected by the differential filter. For example, when a Log filter is used as the differential filter, a value, by which the Log filter can detect the pseudo-vein pattern, is contained in the parameter storage area. In this case, the value of the parameter to be contained is equal to or greater than 2.0.

The above-mentioned vein data configuration can be applied to, for example, a non-contact IC chip, or an IC card, such as a Subscriber Identity Module (SIM) card, used in a mobile telephone and the like. In addition, this vein data configuration can be applied to a recording medium, such as a DVD medium, a HD-DVD medium, a Blu-ray medium, CompactFlash (registered trademark), a memory stick, or a SD memory card.

It should be understood by those skilled in the art that various modifications, combinations, sub-combinations and alterations may occur depending on design requirements and other factors insofar as they are within the scope of the appended claims or the equivalents thereof.

For example, although in the above-mentioned embodiments, it has been described that a vein pattern registration apparatus 20 and a vein pattern authentication apparatus 30 are separately provided, respectively, a vein pattern management apparatus including functions of both a vein pattern registration apparatus 20 and a vein pattern authentication apparatus 30 may be provided.

Furthermore, although in the above-mentioned embodiments, it has been described that a transmissive imaging unit is provided each of a vein pattern registration apparatus 20 and a vein pattern authentication apparatus 30, a reflective imaging unit may be provided depending on a portion of a body surface to be captured.

The invention claimed is:

1. A vein pattern management system for registering and authenticating a vein pattern acquired by radiating light to a portion of a living body, comprising:
   an imaging unit for capturing an image of a body surface of the portion of the living body with near-infrared light and generating near-infrared light imaging data;
   a vein pattern extraction unit for extracting a vein pattern from the near-infrared light imaging data by applying a differential filter, which outputs a large value for a pixel having a large difference between the pixel and its surrounding pixel, to a plurality of pixels constituting the near-infrared light imaging data;
   a pseudo-vein pattern determination unit for determining presence of a pseudo-vein pattern intentionally formed on a part of the captured body surface based on the extracted vein pattern;
   a vein pattern registration unit for registering the near-infrared light vein pattern based on a determination result from the determination unit to generate a registered vein pattern; and
   a vein pattern authentication unit for comparing a newly generated near-infrared light vein pattern with the registered vein pattern based on the determination result from the pseudo-vein pattern determination unit and authenticating the newly generated near-infrared vein pattern, wherein
   the vein pattern extraction unit calculates a distribution of output values based on acquired output values of the differential filter, and
   the pseudo-vein pattern determination unit determines the presence of the pseudo-vein pattern based on the distribution of the output values.

2. The vein pattern management system according to claim 1, wherein
   the vein pattern extraction unit further includes an output estimation value calculation unit for calculating an output estimation value indicating a ratio of a sum of output values, which are more than a predetermined upper output value, among acquired output values of the differential filter relative to a total sum of the acquired output values of the differential filter, and
   the pseudo-vein pattern determination unit determines the presence of the pseudo-vein pattern based on the output estimation value.

3. The vein pattern management system according to claim 2, wherein
   the pseudo-vein pattern determination unit determines that the pseudo-vein pattern is present when the output estimation value is more than a predetermined threshold value, and determines that the pseudo-vein pattern is not present when the output estimation value is less than the predetermined threshold value.

4. The vein pattern management system according to claim 1, wherein
   the differential filter is a derivative filter.

5. The vein pattern management system according to claim 4, wherein
   the differential filter is a Laplacian of Gaussian (Log) filter.

* * * * *